United States Patent
Jordan et al.

(10) Patent No.: US 11,724,987 B2
(45) Date of Patent: *Aug. 15, 2023

(54) COMPOSITIONS AND METHODS OF TREATING RETINAL DISEASE

(71) Applicant: Aldeyra Therapeutics, Inc., Lexington, MA (US)

(72) Inventors: Thomas A. Jordan, Lexington, MA (US); John E. Dowling, Boston, MA (US); John Clifford Chabala, Scotch Plains, NJ (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 78 days.

This patent is subject to a terminal disclaimer.

(21) Appl. No.: 17/164,556

(22) Filed: Feb. 1, 2021

(65) Prior Publication Data

US 2021/0269402 A1  Sep. 2, 2021

Related U.S. Application Data

(63) Continuation of application No. 16/241,851, filed on Jan. 7, 2019, now Pat. No. 10,913,722, which is a continuation of application No. 15/861,332, filed on Jan. 3, 2018, now Pat. No. 10,202,348, which is a continuation of application No. 15/488,205, filed on Apr. 14, 2017, now Pat. No. 9,896,419, which is a continuation of application No. 15/049,890, filed on Feb. 22, 2016, now Pat. No. 9,650,342, which is a continuation of application No. 14/581,462, filed on Dec. 23, 2014, now Pat. No. 9,265,759, which is a continuation of application No. 13/175,218, filed on Jul. 1, 2011, now Pat. No. 8,940,721, which is a continuation of application No. 11/441,848, filed on May 26, 2006, now Pat. No. 7,973,025.

(60) Provisional application No. 60/723,577, filed on Oct. 4, 2005, provisional application No. 60/685,460, filed on May 26, 2005.

(51) Int. Cl.
| | | |
|---|---|---|
| A61K 31/4418 | (2006.01) |
| A61K 31/41 | (2006.01) |
| A61K 31/423 | (2006.01) |
| C07D 215/38 | (2006.01) |
| A61K 31/44 | (2006.01) |
| A61K 31/426 | (2006.01) |
| A61K 31/435 | (2006.01) |
| A61K 31/4706 | (2006.01) |
| C07C 215/68 | (2006.01) |
| C07C 229/60 | (2006.01) |
| C07D 277/40 | (2006.01) |
| C07D 277/56 | (2006.01) |
| C07D 261/06 | (2006.01) |
| C07D 275/00 | (2006.01) |
| C07D 333/04 | (2006.01) |
| C07C 229/56 | (2006.01) |
| A61K 31/47 | (2006.01) |

(52) U.S. Cl.
CPC ............ *C07D 215/38* (2013.01); *A61K 31/41* (2013.01); *A61K 31/423* (2013.01); *A61K 31/426* (2013.01); *A61K 31/435* (2013.01); *A61K 31/44* (2013.01); *A61K 31/4418* (2013.01); *A61K 31/47* (2013.01); *A61K 31/4706* (2013.01); *C07C 215/68* (2013.01); *C07C 229/56* (2013.01); *C07C 229/60* (2013.01); *C07D 261/06* (2013.01); *C07D 275/00* (2013.01); *C07D 277/40* (2013.01); *C07D 277/56* (2013.01); *C07D 333/04* (2013.01)

(58) Field of Classification Search
CPC ... A61K 31/41; A61K 31/423; A61K 31/4418
See application file for complete search history.

(56) References Cited

U.S. PATENT DOCUMENTS

| | | |
|---|---|---|
| 2,086,186 A | 7/1937 | Messer |
| 3,912,748 A | 10/1975 | Evans et al. |
| 4,668,626 A | 5/1987 | Kobayashi et al. |
| 4,956,351 A | 9/1990 | Mesens et al. |
| 5,024,998 A | 6/1991 | Bodor |
| 5,364,637 A | 11/1994 | De et al. |
| 5,376,645 A | 12/1994 | Stella et al. |
| 5,419,898 A | 5/1995 | Ikejiri et al. |
| 5,472,954 A | 12/1995 | Loftsson |
| 5,493,027 A | 2/1996 | Nichols et al. |
| 5,576,311 A | 11/1996 | Guy |
| 5,668,117 A | 9/1997 | Shapiro |

(Continued)

FOREIGN PATENT DOCUMENTS

| | | |
|---|---|---|
| CA | 3032609 A1 | 3/2018 |
| CN | 1882339 A | 12/2006 |

(Continued)

OTHER PUBLICATIONS

Abelson and Spitalny, "Combined analysis of two studies using the conjunctival allergen challenge model to evaluate olopatadine hydrochloride, a new ophthalmic antiallergic agent with dual activity," Am J Ophthalmol. 1998;125(6):797-804.

(Continued)

*Primary Examiner* — Barbara P Badio
(74) *Attorney, Agent, or Firm* — Dechert LLP; Andrea L. C. Reid; Kiruthika Elamparuthi

(57) ABSTRACT

Compositions and methods for treating macular degeneration and other forms of retinal disease whose etiology involves the accumulation of A2E and/or lipofuscin, and, more specifically, for preventing the formation and/or accumulation of A2E are disclosed.

9 Claims, 7 Drawing Sheets

(56) References Cited

U.S. PATENT DOCUMENTS

| | | |
|---|---|---|
| 5,767,109 A | 6/1998 | Sanchez et al. |
| 5,998,488 A | 12/1999 | Shinohara et al. |
| 6,107,300 A | 8/2000 | Bakthavatchalam et al. |
| 6,191,127 B1 | 2/2001 | Holscher et al. |
| 6,358,948 B1 | 3/2002 | Zhang et al. |
| 6,444,221 B1 | 9/2002 | Shapiro |
| 6,492,520 B1 | 12/2002 | Chen |
| 6,498,154 B1 | 12/2002 | Grubb et al. |
| 6,515,010 B1 | 2/2003 | Franchini et al. |
| 6,525,056 B2 | 2/2003 | Arvanitis et al. |
| 6,569,879 B2 | 5/2003 | Liu et al. |
| 7,083,803 B2 | 8/2006 | Peyman |
| 7,297,709 B2 | 11/2007 | Dai et al. |
| 7,531,564 B2 | 5/2009 | Malamas et al. |
| 7,842,312 B2 | 11/2010 | Burgermeister et al. |
| 7,973,025 B2 | 7/2011 | Jordan et al. |
| 7,982,071 B2 | 7/2011 | Scott et al. |
| 8,158,609 B1 | 4/2012 | Marsh et al. |
| 8,435,965 B2 | 5/2013 | Tabuchi et al. |
| 8,575,221 B2 | 11/2013 | Masse et al. |
| 8,722,669 B2 | 5/2014 | Palczewski et al. |
| 8,791,154 B2 | 7/2014 | Gamache et al. |
| 8,940,721 B2 | 1/2015 | Jordan et al. |
| 8,940,764 B2 | 1/2015 | Jordan et al. |
| 9,067,963 B2 | 6/2015 | Thompson et al. |
| 9,259,427 B2 | 2/2016 | Tierney et al. |
| 9,265,759 B2 | 2/2016 | Jordan et al. |
| 9,364,471 B2 | 6/2016 | Jordan et al. |
| 9,375,408 B2 | 6/2016 | Singh |
| 9,604,997 B2 | 3/2017 | Jordan et al. |
| 9,650,342 B2 | 5/2017 | Jordan et al. |
| 9,687,481 B2 | 6/2017 | Brady et al. |
| 9,814,701 B2 | 11/2017 | Jordan et al. |
| 9,896,419 B2 | 2/2018 | Jordan et al. |
| 10,058,095 B2 | 8/2018 | Czarnik |
| 10,111,862 B2 | 10/2018 | Chabala et al. |
| 10,202,348 B2 | 2/2019 | Jordan et al. |
| 10,213,395 B2 | 2/2019 | Brady et al. |
| 10,414,732 B2 | 9/2019 | Buist et al. |
| 10,426,790 B2 | 10/2019 | Young et al. |
| 10,543,181 B2 | 1/2020 | Brady et al. |
| 10,550,085 B2 | 2/2020 | Brady et al. |
| 10,588,874 B2 | 3/2020 | Brady et al. |
| 10,913,722 B2 | 2/2021 | Jordan et al. |
| 11,007,157 B2 | 5/2021 | Brady et al. |
| 11,040,039 B2 | 6/2021 | Macdonald et al. |
| 11,046,650 B2 | 6/2021 | Brady et al. |
| 11,129,823 B2 | 9/2021 | Brady et al. |
| 11,197,821 B2 | 12/2021 | Clark et al. |
| 11,459,300 B2 | 10/2022 | Brady et al. |
| 2004/0132636 A1 | 7/2004 | Dooley et al. |
| 2004/0198828 A1 | 10/2004 | Abelson et al. |
| 2004/0235892 A1 | 11/2004 | Dai et al. |
| 2005/0020603 A1 | 1/2005 | Dai et al. |
| 2005/0090553 A1 | 4/2005 | Shapiro |
| 2005/0130906 A1 | 6/2005 | Matier et al. |
| 2005/0197292 A1 | 9/2005 | Smithson et al. |
| 2005/0234018 A1 | 10/2005 | Lyons et al. |
| 2006/0014786 A1 | 1/2006 | Raut |
| 2006/0111318 A1 | 5/2006 | Okamoto |
| 2006/0183909 A1 | 8/2006 | Schmitt et al. |
| 2006/0189608 A1 | 8/2006 | Bingaman |
| 2006/0257488 A1 | 11/2006 | Hubbard |
| 2007/0129404 A1 | 6/2007 | Hagihara et al. |
| 2007/0135481 A1 | 6/2007 | Jordan et al. |
| 2007/0243257 A1 | 10/2007 | Bedos et al. |
| 2007/0297981 A1 | 12/2007 | Ousler et al. |
| 2008/0108818 A1 | 5/2008 | Chen et al. |
| 2008/0241256 A1 | 10/2008 | Kuhn |
| 2009/0118503 A1 | 5/2009 | Sprott et al. |
| 2009/0182009 A1 | 7/2009 | Jordan et al. |
| 2010/0160304 A1 | 6/2010 | Katayama |
| 2010/0240624 A1 | 9/2010 | Chapin et al. |
| 2010/0331315 A1 | 12/2010 | Haddach et al. |
| 2011/0071091 A1 | 3/2011 | Chowhan et al. |
| 2011/0105450 A1 | 5/2011 | Chapin et al. |
| 2011/0257271 A1 | 10/2011 | Masse et al. |
| 2011/0263645 A1 | 10/2011 | Jordan et al. |
| 2012/0108585 A1 | 5/2012 | Vu |
| 2012/0295967 A1 | 11/2012 | Gamache et al. |
| 2012/0302601 A1 | 11/2012 | Jordan et al. |
| 2013/0165419 A1 | 6/2013 | Lindstrom et al. |
| 2013/0190500 A1 | 7/2013 | Greiner et al. |
| 2014/0038918 A1 | 2/2014 | Rodriguez-Boulan et al. |
| 2014/0050797 A1 | 2/2014 | Venkatesh et al. |
| 2014/0235604 A1 | 8/2014 | Palczewski et al. |
| 2014/0235722 A1 | 8/2014 | Jordine et al. |
| 2015/0209333 A1 | 7/2015 | Jordan et al. |
| 2015/0209345 A1 | 7/2015 | Jordan et al. |
| 2015/0258120 A1 | 9/2015 | Zarnitsyn et al. |
| 2015/0335632 A1 | 11/2015 | Brady et al. |
| 2015/0344432 A1 | 12/2015 | Jordan et al. |
| 2015/0344447 A1 | 12/2015 | Chabala et al. |
| 2016/0009698 A1 | 1/2016 | Julia Jane et al. |
| 2016/0052930 A1 | 2/2016 | Fensome et al. |
| 2016/0151381 A1 | 6/2016 | Blackburn et al. |
| 2016/0168098 A1 | 6/2016 | Jordan et al. |
| 2017/0029354 A1 | 2/2017 | Singh |
| 2017/0095449 A1 | 4/2017 | Winters et al. |
| 2017/0143627 A1 | 5/2017 | Misra |
| 2017/0239196 A1 | 8/2017 | Brady et al. |
| 2017/0266220 A1 | 9/2017 | Young et al. |
| 2017/0320829 A1 | 11/2017 | Jordan et al. |
| 2017/0354655 A1 | 12/2017 | Beaupre et al. |
| 2018/0050989 A1 | 2/2018 | Machatha et al. |
| 2018/0092882 A1 | 4/2018 | Jordan et al. |
| 2018/0194733 A1 | 7/2018 | Jordan et al. |
| 2018/0235980 A1 | 8/2018 | Shah |
| 2018/0250306 A1 | 9/2018 | Brady et al. |
| 2018/0265474 A1 | 9/2018 | Buist et al. |
| 2018/0354905 A1 | 12/2018 | Brady et al. |
| 2019/0105322 A1 | 4/2019 | Macdonald et al. |
| 2019/0125729 A1 | 5/2019 | Chabala et al. |
| 2019/0183878 A1 | 6/2019 | Brady et al. |
| 2019/0210971 A1 | 7/2019 | Jordan et al. |
| 2019/0231715 A1 | 8/2019 | Brady et al. |
| 2019/0247334 A1 | 8/2019 | Brady et al. |
| 2020/0038392 A1 | 2/2020 | Brady et al. |
| 2020/0062712 A1 | 2/2020 | Machatha et al. |
| 2020/0121591 A1 | 4/2020 | Clark et al. |
| 2020/0199075 A1 | 6/2020 | Brady et al. |
| 2020/0246345 A1 | 8/2020 | Brady et al. |
| 2020/0323841 A1 | 10/2020 | Clark et al. |
| 2020/0368182 A1 | 11/2020 | Brady et al. |

FOREIGN PATENT DOCUMENTS

| | | |
|---|---|---|
| CN | 101048384 A | 10/2007 |
| CN | 101321742 A | 12/2008 |
| CN | 101534826 A | 9/2009 |
| CN | 101611009 A | 12/2009 |
| CN | 104884049 A | 9/2015 |
| CN | 105120866 A | 12/2015 |
| EP | 0186367 A2 | 7/1986 |
| EP | 0245054 A1 | 11/1987 |
| EP | 0483881 A1 | 5/1992 |
| EP | 1621199 A1 | 2/2006 |
| EP | 1679308 A1 | 7/2006 |
| EP | 1888548 A1 | 2/2008 |
| EP | 2301549 A1 | 3/2011 |
| GB | 2327672 A | 2/1999 |
| JP | 06239748 | 8/1994 |
| JP | 07025758 | 1/1995 |
| JP | 09169647 | 6/1997 |
| JP | 2001041757 A | 2/2001 |
| JP | 2002003364 A | 1/2002 |
| JP | 2005132834 A | 5/2005 |
| JP | 2005187407 A | 7/2005 |
| JP | 3736916 B2 | 1/2006 |
| JP | 2006008568 A | 1/2006 |
| JP | 2007532648 A | 11/2007 |
| JP | 2008542291 A | 11/2008 |
| JP | 4466875 B2 | 5/2010 |
| JP | 4748289 B2 | 8/2011 |

(56) References Cited

FOREIGN PATENT DOCUMENTS

| | | |
|---|---|---|
| JP | 2012506449 A | 3/2012 |
| JP | 5194218 B2 | 5/2013 |
| JP | 2014515355 A | 6/2014 |
| JP | 2015057437 A | 3/2015 |
| JP | 2015535293 A | 12/2015 |
| RU | 2010137842 A | 3/2012 |
| RU | 2565448 C2 | 10/2015 |
| SU | 50906 A1 | 11/1936 |
| WO | WO-199507274 A1 | 3/1995 |
| WO | WO-1996022992 A1 | 8/1996 |
| WO | WO-1998005645 A1 | 2/1998 |
| WO | WO-1999046237 A1 | 9/1999 |
| WO | WO-2001041757 A1 | 6/2001 |
| WO | WO-2004082622 A2 | 9/2004 |
| WO | WO-2004091630 A1 | 10/2004 |
| WO | WO-2005035506 A1 | 4/2005 |
| WO | WO-2005040151 A1 | 5/2005 |
| WO | WO-2005051328 A2 | 6/2005 |
| WO | WO-2005079774 A2 | 9/2005 |
| WO | WO-2005105067 A2 | 11/2005 |
| WO | WO-2006000421 A2 | 1/2006 |
| WO | WO-2006002473 A1 | 1/2006 |
| WO | WO-2006049968 A1 | 5/2006 |
| WO | WO-2006077821 A1 | 7/2006 |
| WO | WO-2006127945 A1 | 11/2006 |
| WO | WO-2007118276 A1 | 10/2007 |
| WO | WO-2008014602 A1 | 2/2008 |
| WO | WO-2009045479 A1 | 4/2009 |
| WO | WO-2009102418 A1 | 8/2009 |
| WO | WO-2010048332 A2 | 4/2010 |
| WO | WO-2010133672 A1 | 11/2010 |
| WO | WO-2011008202 A1 | 1/2011 |
| WO | WO-2011071995 A2 | 6/2011 |
| WO | WO-2011072141 A1 | 6/2011 |
| WO | WO-2011078204 A1 | 6/2011 |
| WO | WO-2012097173 A2 | 7/2012 |
| WO | WO-2012105887 A1 | 8/2012 |
| WO | WO-2014100425 A1 | 6/2014 |
| WO | WO-2014116593 A1 | 7/2014 |
| WO | WO-2014116836 A2 | 7/2014 |
| WO | WO-2015002893 A1 | 1/2015 |
| WO | WO-2015187942 A1 | 12/2015 |
| WO | WO-2016085939 A2 | 6/2016 |
| WO | WO-2016165626 A1 | 10/2016 |
| WO | WO-2017035077 A1 | 3/2017 |
| WO | WO-2017035082 A1 | 3/2017 |
| WO | WO-2017147617 A1 | 8/2017 |
| WO | WO-2017196881 A1 | 11/2017 |
| WO | WO-2017214201 A1 | 12/2017 |
| WO | WO-2018039192 A1 | 3/2018 |
| WO | WO-2018039197 A1 | 3/2018 |
| WO | WO-2018064354 A1 | 4/2018 |
| WO | WO-2018067860 A1 | 4/2018 |
| WO | WO-2018170476 A1 | 9/2018 |
| WO | WO-2019075136 A1 | 4/2019 |
| WO | WO-2020018498 A1 | 1/2020 |
| WO | WO-2020028820 A1 | 2/2020 |
| WO | WO-2020033344 A1 | 2/2020 |
| WO | WO-2020068986 A1 | 4/2020 |
| WO | WO-2020072621 A1 | 4/2020 |
| WO | WO-2020118045 A1 | 6/2020 |
| WO | WO-2020198064 A1 | 10/2020 |
| WO | WO-2020223685 A1 | 11/2020 |
| WO | WO-2020223717 A1 | 11/2020 |
| WO | WO-2021195211 A | 9/2021 |
| WO | WO-2021231792 A1 | 11/2021 |
| WO | WO-2021248031 A1 | 12/2021 |

OTHER PUBLICATIONS

Abelson et al., "Conjunctival allergen challenge. A clinical approach to studying allergic conjunctivitis," Arch Ophthalmol. 1990;108(1):84-8.

Abelson et al., "The conjunctival provocation test model of ocular allergy: utility for assessment of an ocular corticosteroid, loteprednol etabonate," J Ocul Pharmacol Ther. 1998;14(6):533-42.

Abramovitz et al., "The utilization of recombinant prostanoid receptors to determine the affinities and selectivities of prostaglandins and related analogs," Biochim Biophys Acta. 2000;1483(2):285-93.

Ackerman et al., "Ocular itch associated with allergic conjunctivitis: latest evidence and clinical management," Ther Adv Chronic Dis. 2016;7(1):52-67.

Acland et al., "Gene therapy restores vision in a canine model of childhood blindness," Nat Genet. 2001;28(1):92-5.

Aharony et al., "Pharmacological characterization of cloned human NK-2 (neurokinin A) receptor expressed in a baculovirus/Sf-21 insect cell system," Mol Pharmacol. 1993;44(2):356-63.

Aktürk et al., "Nitric oxide and malondialdehyde levels in plasma and tissue of psoriasis patients," J Eur Acad Dermatol Venereol. 2012;26(7):833-7.

Al-Bari, "Chloroquine analogues in drug discovery: new directions of uses, mechanisms of actions and toxic manifestations from malaria to multifarious diseases," J Antimicrob Chemother. 2015;70(6):1608-21.

Al-Essa et al., "Clinical, fluorine-18 labeled 2-fluoro-2-deoxyglucose positron emission tomography (FDG PET), MRI of the brain and biochemical observations in a patient with 4-hydroxybutyric aciduria; a progressive neurometabolic disease," Brain Dev. 2000;22(2):127-31.

Al-Hasani et al., "Phosphoryl exchange is involved in the mechanism of the insulin receptor kinase," FEBS Lett. 1994;349(1):17-22.

Albano et al., "Immune response towards lipid peroxidation products as a predictor of progression of non-alcoholic fatty liver disease to advanced fibrosis," Gut. 2005;54(7):987-93.

Aldeyra Therapeutics, "Aldeyra Therapeutics Announces Collaboration With the National Organization for Rare Disorders to Enhance Awareness for Sjogren-Larsson Syndrome Patients," Press Release. 2014.

Aldeyra Therapeutics, "Aldeyra Therapeutics Announces Positive Mesothelioma Investigator-Sponsored Clinical Trial Results Presented at The International Association for The Study of Lung Cancer 19th World Conference on Lung Cancer," Press Release. 2018.

Aldeyra Therapeutics, "Aldeyra Therapeutics Announces Positive Results from Dry Eye Disease Phase 2a Clinical Trial," Press Release. 2017.

Aldeyra Therapeutics, "Aldeyra Therapeutics Announces Positive Results from Phase 2b Dry Eye Disease Clinical Trial," Press Release. 2018.

Aldeyra Therapeutics, "Aldeyra Therapeutics Announces Positive Top-Line Results from the Phase 3 ALLEVIATE Trial in Patients with Allergic Conjunctivitis," Press Release. 2019.

Aldeyra Therapeutics, "Aldeyra Therapeutics Announces Presentation of Novel Data on the Efficacy of ADX-102 in a Medel of Succinic Semialdehyde Dehydrogenase Activity at the 2017 American Society of Human Genetics Annual Meeting," Press Release. 2017.

Aldeyra Therapeutics, "Aldeyra Therapeutics Announces Presentation of Phase 2 Allergic Conjunctivitis Results at the 2016 American College of Allergy, Asthma and Immunology Annual Scientific Meeting," Press Release. 2016.

Aldeyra Therapeutics, "Aldeyra Therapeutics Announces Presentation of Results on the Efficacy of ADX-102 in Noninfectious Anterior Uveitis at the American Uveitis Society Held at the American Academy of Ophthalmology 2017 Annual Meeting," Press Release. 2017.

Aldeyra Therapeutics, "Aldeyra Therapeutics Announces Results from Allergic Conjunctivitis Phase 2b Clinical Trial and Plans for Phase 3 Clinical Testing," Press Release. 2017.

Aldeyra Therapeutics, "Aldeyra Therapeutics Announces Third Quarter 2017 Financial Results," Press Release. 2017.

Aldeyra Therapeutics, "Aldeyra Therapeutics Launches the Aldeyra Registry for Patients with Sjögren-Larsson Syndrome," Press Release. 2017.

(56) References Cited

OTHER PUBLICATIONS

Aldeyra Therapeutics, "Aldeyra Therapeutics Opens Enrollment in Noninfectious Anterior Uveitis Phase II Clinical Trial," Press Release. 2015.

Aldeyra Therapeutics, "Aldeyra Therapeutics Opens Enrollment in Sjogren-Larsson Syndrome Clinical Trial and Finalizes Noninfectious Anterior Uveitis Clinical Trial Protocol," Press Release. 2015.

Aldeyra Therapeutics, "Aldeyra Therapeutics Presents Dry Eye Disease Phase 2a Clinical Trial Results at the Association for Research in Vision and Ophthalmology 2018 Annual Meeting," Press Release. 2018.

Aldeyra Therapeutics, "Aldeyra Therapeutics Presents Evidence for Aldehyde Sequestration as a Potential Therapeutic Approach in Succinic Semialdehyde Dehydrogenase Deficiency at the American Society of Human Genetics 2017 Annual Meeting," Press Release. 2017.

Aldeyra Therapeutics, "Aldeyra Therapeutics Presents Noninfectious Anterior Uveitis Phase 2 Clinical Trial Data at the Association for Research in Vision and Ophthalmology 2017 Annual Meeting," Press Release. 2017.

Aldeyra Therapeutics, "Aldeyra Therapeutics Presents Noninfectious Anterior Uveitis Phase 2 Clinical Trial Data to the American Uveitis Society Held at the American Academy of Ophthalmology 2017 Annual Meeting," Press Release. 2017.

Aldeyra Therapeutics, "Aldeyra Therapeutics Provides Update on Late-Stage Clinical Trials at 2016 Research and Development Day," Press Release. 2016.

Aldeyra Therapeutics, "Aldeyra Therapeutics Provides Update on NS2 Clinical Program," Press Release. 2015.

Aldeyra Therapeutics, "Aldeyra Therapeutics Provides Update on Ophthalmic Programs at 2019 Research & Development Day," Press Release. 2019.

Aldeyra Therapeutics, "Aldeyra Therapeutics Reaches Agreement with the US Food and Drug Administration for the Use of RASP as an Objective Sign for the Treatment of Dry Eye Disease," Press Release. 2020.

Aldeyra Therapeutics, "Aldeyra Therapeutics Schedules Conference Call and Webcast to Announce Results from Allergic Conjunctivitis Phase 2b Clinical Trial," Press Release. 2017.

Aldeyra Therapeutics, "Aldeyra Therapeutics Schedules Conference Call to Present Results of a Randomized, Double-Blind, Vehicle-Controlled Clinical Trial in Sjogren-Larsson Syndrome," Press Release. 2016.

Aldeyra Therapeutics, "Aldeyra Therapeutics Schedules Webcast and Conference Call to Announce Results from Dry Eye Disease Phase 2a Clinical Trial," Press Release. 2017.

Aldeyra Therapeutics, "Aldeyra Therapeutics Selected for Podium Presentation of Phase 2a Dry Eye Disease Results at the 2018 Association for Research in Vision and Ophthalmology (ARVO) Annual Meeting," Press Release. 2018.

Aldeyra Therapeutics, "Aldeyra Therapeutics Submits FDA IND Filing for Noninfectious Anterior Uveitis," Press Release. 2014.

Aldeyra Therapeutics, "Aldeyra Therapeutics Submits IND Filing to FDA for Clinical Testing of NS2 in Patients With Sjogren-Larsson Syndrome," Press Release. 2015.

Aldeyra Therapeutics, "Aldeyra Therapeutics to Host 2019 Research & Development Day," Press Release. 2019.

Aldeyra Therapeutics, "Aldeyra Therapeutics to Present at the 2016 SSADH Symposium," Press Release. 2016.

Aldeyra Therapeutics, "Aldeyra Therapeutics to Present Novel Data on a Potential Treatment for Sjogren-Larsson Syndrome at the 2015 Society for Inherited Metabolic Disorders Annual Meeting," Press Release. 2015.

Aldeyra Therapeutics, "Aldeyra Therapeutics to Present Novel Data on a Potential Treatment for Succinic Semi-Aldehyde Dehydrogenase Deficiency at the 2015 American Society of Human Genetics (ASHG) Annual Meeting," Press Release. 2015.

Aldeyra Therapeutics, "Aldeyra Therapeutics' Data on Lead Candidate NS2 to be Presented at Society for Investigative Dermatology 2014 Annual Meeting," Press Release. 2014.

Aldeyra Therapeutics, "Aldeyra Therapeutics, Inc. Announces Last Patient Dosed in Allergic Conjunctivitis Phase 2b Clinical Trial," Press Release. 2017.

Aldeyra Therapeutics, "Aldeyra Therapeutics, Inc. Announces Last Patient Dosed in Phase II Clinical Trial of Topical Dermatologic NS2 in Patients With Sjögren-Larsson Syndrome," Press Release. 2016.

Aldeyra Therapeutics, "Aldeyra Therapeutics, Inc. Receives Orphan Drug Designation from the U.S. Food and Drug Administration for ADX-102 in Sjögren-Larsson Syndrome," Press Release. 2017.

Aldeyra Therapeutics, "Phase II Allergic Conjunctivitis," Press Release. 2016.

Aldini et al., "Lipoxidation-derived reactive carbonyl species as potential drug targets in preventing protein carbonylation and related cellular dysfunction," ChemMedChem. 2006;1(10):1045-58.

Aldini et al., "The carbonyl scavenger carnosine ameliorates dyslipidaemia and renal function in Zucker obese rats," J Cell Mol Med. 2011;15(6):1339-54.

Amara et al., "Autoantibodies to malondialdehyde-modified epitope in connective tissue diseases and vasculitides," Clin Exp Immunol. 1995;101(2):233-8.

Ao et al., "Methyl-(beta)-Cyclodextrin Impairs the Monocyte-Adhering Ability of Endothelial Cells by Down-Regulating Adhesion Molecules and Caveolae and Reorganizing the Actin Cytoskeleton," Biol Pharm Bull. 2016;39(6):1029-34.

Apparsundaram et al., "Molecular cloning of a human, hemicholinium-3-sensitive choline transporter," Biochem Biophys Res Commun. 2000;276(3):862-7.

Ardati et al., "Interaction of [3H]orphanin FQ and 125I-Tyr14-orphanin FQ with the orphanin FQ receptor: kinetics and modulation by cations and guanine nucleotides," Mol Pharmacol. 1997;51(5):816-24.

Ashton et al., "Location of penetration and metabolic barriers to levobunolol in the corneal epithelium of the pigmented rabbit," J Pharmacol Exp Ther. 1991;259(2):719-24.

Atkinson et al., "Triazaphenanthrenes. Part VI.* Further Observations on the Widman-Stoermer and Brosche Reactions," J Chem Soc C. 1966;2053-60.

Augustin et al., "Oxidative reactions in the tear fluid of patients suffering from dry eyes," Graefes Arch Clin Exp Ophthalmol. 1995;233(11):694-8.

Axelsson et al., "Experimental colitis induced by dextran sulphate sodium in mice: beneficial effects of sulphasalazine and olsalazine," Aliment Pharmacol Ther. 1998;12(9):925-34.

Bachman and Welton, "Quinoline derivatives from 3-nitro-4-hydroxyquinoline," J Am Chem Soc. 1947;69(2):365-71.

Bacsi et al., "Effect of pollen-mediated oxidative stress on immediate hypersensitivity reactions and late-phase inflammation in allergic conjunctivitis," J Allergy Clin Immunol. 2005;116(4):836-43.

Badii, "Allergic Conjunctivitis," Healthline. 2016; Retrieved 2019: https://www.healthline.com/health/allergic-conjunctivitis.

Balci et al., "Effects of computer monitor-emitted radiation on oxidant/antioxidant balance in cornea and lens from rats," Mol Vis. 2009;15:2521-5.

Balci et al., "Investigation of oxidative stress in pterygium tissue," Mol Vis. 2011;17:443-447.

Ballard et al., "Effects of sildenafil on the relaxation of human corpus cavernosum tissue in vitro and on the activities of cyclic nucleotide phosphodiesterase isozymes," J Urol. 1998;159(6):2164-71.

Baltatzis et al., "Mycophenolate mofetil as an immunomodulatory agent in the treatment of chronic ocular inflammatory disorders," Ophthalmology. 2003;110(5):1061-5.

Bardwell et al., "Docking sites on mitogen-activated protein kinase (MAPK) kinases, MAPK phosphatases and the Elk-1 transcription factor compete for MAPK binding and are crucial for enzymic activity," Biochem J. 2003;370(Pt 3):1077-1085.

Baron et al., "[3H]MDL 105,519, a high-affinity radioligand for the N-methyl-D-aspartate receptor-associated glycine recognition site," J Pharmacol Exp Ther. 1996;279(1):62-8.

(56) References Cited

OTHER PUBLICATIONS

Bartoli et al., "Malondialdehyde in exhaled breath condensate as a marker of oxidative stress in different pulmonary diseases," Mediators Inflamm. 2011;2011:891752.

Batista et al., "Age-dependent changes in rat lacrimal gland antioxidant and vesicular related protein expression profiles," Mol Vis. 2012;18:194-202.

Batista et al., "Short-term treatment with bisphenol-A leads to metabolic abnormalities in adult male mice," PLoS One. 2012;7(3):e33814.

Baum et al., "Omega 3 fatty acid inhibition of inflammatory cytokine-mediated Connexin43 regulation in the heart," Front Physiol. 2012;3:272.

Baz et al., "Plasma reactive oxygen species activity and antioxidant potential levels in rosacea patients: correlation with seropositivity to Helicobacter pylori," Int J Dermatol. 2004;43(7):494-7.

Berge et al., "Pharmaceutical salts," J Pharm Sci. 1977;66(1):1-19.

Berkhout et al., "Cloning, in vitro expression, and functional characterization of a novel human CC chemokine of the monocyte chemotactic protein (MCP) family (MCP-4) that binds and signals through the CC chemokine receptor 2B," J Biol Chem. 1997;272(26):16404-13.

Bermudez and Grau, "Thermosensitive poloxamer-based injectables as controlled drug release platforms for veterinary use: Development and in-vitro evaluation," Int Res J Pharm Pharmacol. 2011;1(6):109-118.

Bernstein and Rando, "The specific inhibition of 11-cis-retinyl palmitate formation in the frog eye by diaminophenoxypentane, an inhibitor of rhodopsin regeneration," Vision Res. 1985;25(6):741-8.

Bernstein et al., "Mechanism of action of aromatic amines that short-circuit the visual cycle," Biochemistry. 1986;25(11):3370-7.

Bernstein et al., "Retinal toxicity associated with occupational exposure to the fish anesthetic MS-222," Am J Ophthalmol. 1997;124(6):843-4.

Bernstein et al., "Short-circuiting the visual cycle with retinotoxic aromatic amines," Proc Natl Acad Sci U S A. 1986;83(6):1632-5.

Bickett et al., "A high throughput fluorogenic substrate for interstitial collagenase (MMP-1) and gelatinase (MMP-9)," Anal Biochem. 1993;212(1):58-64.

Bignon et al., "SR146131: a new potent, orally active, and selective nonpeptide cholecystokinin subtype 1 receptor agonist. I. In vitro studies," J Pharmacol Exp Ther. 1999;289(2):742-51.

Boldogh et al., "ROS generated by pollen NADPH oxidase provide a signal that augments antigen-induced allergic airway inflammation," J Clin Invest. 2005;115(8):2169-79.

Bousquet et al., "How to design and evaluate randomized controlled trials in immunotherapy for allergic rhinitis: an ARIA-GA(2) LEN statement," Allergy. 2011;66(6):765-74.

Boyer et al., "Lipofuscin and N-retinylidene-N-retinylethanolamine (A2E) accumulate in retinal pigment epithelium in absence of light exposure: their origin is 11-cis-retinal," J Biol Chem. 2012;287(26):22276-86.

Bozkir et al., "Effect of hydroxypropyl-beta-cyclodextrin on the solubility, stability and in-vitro release of ciprofloxacin for ocular drug delivery," Acta Pol Pharm. 2012;69(4):719-24.

Bragagni et al., "Cyclodextrin complexation highly enhances efficacy of arylsulfonylureido benzenesulfonamide carbonic anhydrase inhibitors as atopical antiglaucoma agents," Bioorg Med Chem. 2015;23(18):6223-7.

Brenneman et al., "Cannabidiol Provides Protection from Ethanol and Ammonium toxicity in a Hippocampal Model of Hepatic Encephalopathy," 24th Annual Symposium of the International Cannabinoid Research Society, Baveno, Italy. 2014;73.

Brenneman et al., "Small molecule anticonvulsant agents with potent in vitro neuroprotection," J Mol Neurosci. 2012;47(2):368-79.

Brewitt and Sistani, "Dry eye disease: the scale of the problem," Surv Ophthalmol. 2001;45 Suppl 2:S199-202.

Brockhaus et al., "Identification of two types of tumor necrosis factor receptors on human cell lines by monoclonal antibodies," Proc Natl Acad Sci U S A. 1990;87(8):3127-31.

Brown, "3H-batrachotoxinin-A benzoate binding to voltage-sensitive sodium channels: inhibition by the channel blockers tetrodotoxin and saxitoxin," J Neurosci. 1986;6(7):2064-70.

Brozek et al., "Grading quality of evidence and strength of recommendations in clinical practice guidelines: Part 2 of 3. The GRADE approach to grading quality of evidence about diagnostic tests and strategies," Allergy. 2009;64(8):1109-16.

Bryant et al., "A novel class of 5-HT2A receptor antagonists: aryl aminoguanidines," Life Sci. 1996;59(15):1259-68.

Bucciantini et al., "Inherent toxicity of aggregates implies a common mechanism for protein misfolding diseases," Nature. 2002;416(6880):507-11.

Buchan et al., "Characterization of three non-peptide endothelin receptor ligands using human cloned ETA and ETB receptors," Br J Pharmacol. 1994;112(4):1251-7.

Buddi et al., "Evidence of oxidative stress in human corneal diseases," J Histochem Cytochem. 2002;50(3):341-51.

Burcham et al., "Aldehyde-sequestering drugs: tools for studying protein damage by lipid peroxidation products," Toxicology. 2002;181-182:229-36.

Burstein, "Preservative cytotoxic threshold for benzalkonium chloride and chlorhexidine digluconate in cat and rabbit corneas," Invest Ophthalmol Vis Sci. 1980;19(3):308-13.

Burstein, "The effects of topical drugs and preservatives on the tears and corneal epithelium in dry eye," Trans Ophthalmol Soc U K (1962). 1985;104(Pt 4):402-9.

Canonica et al., "Recommendations for standardization of clinical trials with Allergen Specific Immunotherapy for respiratory allergy. A statement of a World Allergy Organization (WAO) taskforce," Allergy. 2007;62(3):317-24.

Canonica et al., "Sub-lingual immunotherapy: World Allergy Organization Position Paper 2009," Allergy. 2009;64 Suppl 91:1-59.

Casanaro et al., "A convenient solvent system for cellulose dissolution and derivatization: Mechanistic aspects of the acylation of the biopolymer in tetraallylammonium fluoride/dimethyl sulfoxide," Carbohydr Polym. 2011;8(3):1395-402.

Cejková et al., "The role of conjunctival epithelial cell xanthine oxidoreductase/xanthine oxidase in oxidative reactions on the ocular surface of dry eye patients with Sjögren's syndrome," Histol Histopathol. 2007;22(9):997-1003.

Chapple et al., "Unfolding retinal dystrophies: a role for molecular chaperones?" Trends Mol Med. 2001;7(9):414-21.

Cheng et al., "A synthetic peptide derived from p34cdc2 is a specific and efficient substrate of src-family tyrosine kinases," J Biol Chem. May 5, 1992;267(13):9248-56.

Chiarpotto et al., "Role of 4-hydroxy-2,3-nonenal in the pathogenesis of fibrosis," Biofactors. 2005;24(1-4):229-36.

Chicchi et al., "Alterations in receptor activation and divalent cation activation of agonist binding by deletion of intracellular domains of the glucagon receptor," J Biol Chem. 1997;272(12):7765-9.

Conover et al., "Thiazole Analogs of Pyridoxine," Journal of the American Chemical Society, 72(11):5221-5225 (1950).

Davies, "Biopharmaceutical considerations in topical ocular drug delivery," Clin Exp Pharmacol Physiol, 2000; 27(7):558-62.

De Jong, "Age-Related Macular Degeneration," N Engl J Med, 355(14):1474-1485 (2006).

Demir et al., "The protective effect of alpha-lipoic acid against oxidative damage in rabbit conjunctiva and cornea exposed to ultraviolet radiation," Ophthalmologica, 2005; 219(1):49-53.

Dolmotova et al., "Cardiomyocyte ATP release through pannexin 1 aids in early fibroblast activation," Am. J. Physiol Heart Circ Physiol 303(10):H1208-1218 (2012).

Dowling, "Neural and Photochemical Mechanisms of Visual Adaptation in the Rat," Journal of General Physiology, 46(6):1287-1291 (1963).

Drysdale et al., "Complex Promoter and Coding Region Beta 2-adrenergic Receptor Haplotypes Alter Receptor Expression and Predict in vivo Responsiveness," Proc Natl Acad Sci USA, 97(19):10483-10488 (2000).

(56) References Cited

OTHER PUBLICATIONS

EP Supplementary Partial European Search Report from 14743711.5, dated Jul. 20, 2016.
Escalera et al., "Succinic semialdehyde dehydrogenase deficiency: decrease in 4-OH-butyric acid levels with low doses of vigabatrin," An Pediatr (Barc). 72(2):128-32 (2010).
Esterbauer et al., "Chemistry and Biochemistry of 4-Hydroxynonenal, Malonaldehyde and Related Aldehydes," Free Radic Biol Med, 1991; 11:81-128.
Feighner et al., "Receptor for motilin identified in the human gastrointestinal system," Science, 284:2184-2188 (1999).
Fernandes et al., "Characterization of angiotensin-converting enzymes 1 and 2 in the soleus and plantaris muscles of rats," Braz J Med Biol Res., 43:837-842 (2010).
Ferry et al., "Binding of prostaglandins to human PPAR?: Tool assessment and new natural ligands," Eur. J. Pharmacol., 417:77-89 (2001).
Feve et al., "Transcriptional down-regulation by insulin of the beta 3-adrenergic receptor expression in 3T3-F442A adipocytes: a mechanism for repressing the cAMP signaling pathway," Proc Natl Acad Sci USA. 91:5677 (1994).
Fiske et al., "The Colormetric Determination of Phosphorus," J. Biol. Chem., 66:375-400 (1925).
Fitzmaurice et al., "Aldehyde dehydrogenase inhibition as a pathogenic mechanism in Parkinson disease," Proc. Natl Acad Sci U.S.A, 110(2):636-641 (2013).
Ford et al., "Pharmacological pleiotropism of the human recombinant alpha1A-adrenoceptor: implications for alpha1-adrenoceptor classification," Brit. J. Pharmacol., 121:1127-1135 (1997).
Fowler et al., "Coloured Complexes of all-trans-retinal with Benzocaine and Other Local Anesthetics," J Photochem Photobiol B, 8(2):183-188 (1991).
Frantz et al., "The Activation State of p38 Mitogen-Activated Protein Kinase Determines the Efficiency of ATP Competition for Pyridinylimidazole Inhibitor Binding," Biochemistry, 37:13846-13853 (1998).
Friesen et al., "Optimization of a Tertiary Alcohol Series of Phosphodiesterase-4 (PDE4) Inhibitors: Structure-Activity Relationship Related to PDE4 Inhibition and Human Ether-a-go-go Related Gene Potassium Channel Binding Affinity," J. Med. Chem., 46(12):2413-2426 (2003).
Fuchs et al., "Functional characterization of three mutations of the endothelin B receptor gene in patients with Hirschsprung's disease: evidence for selective loss of Gi coupling," Mol. Med., 7:115-124 (2001).
Fukunaga et al., "Single nucleotide polymorphism of human platelet-activating factor receptor impairs G-protein activation," J. Biol. Chem., 276:43025-43030 (2001).
Full 1H NMR assignment for RAL-NS2 in CDCIJ, submitted to Japanese Patent Office Mar. 1, 2012.
Ganapathy et al., "Molecular and ligand-binding characterization of the sigma-receptor in the Jurkat human T lymphocyte cell line," JPET, 289:251-260 (1999).
Gasper et al., "2-Hydroxypropyl-beta-cyclodextrin (HPβCD) reduces age-related lipofuscin accumulation through a cholesterol-associated pathway," Scientific Reports, 2017; 7(2197):1-7.
Gibson et al., "Stable isotope dilution analysis of 4-hydroxybutyric acid: an accurate method for quantification in physiological fluids and the prenatal diagnosis of 4-hydroxybutyric aciduria," Biomed Environ Mass Spectrom., 19(2):89-93 (1990).
Gibson et al., "Stable-isotope dilution analysis of D- and L-2-hydroxyglutaric acid: application to the detection and prenatal diagnosis of D- and L-2-hydroxyglutaric acidemias," Pediatr Res., 34(3):277-80 (1993).
Gibson et al., "The Aldehyde Trap NS2 Mitigates Dense Haze in a Rabbit Model of Photorefractive Keratectomy" ARVO Annual Meeting Abstract, 1 page (Jun. 2015).
Godard et al., "Sur les orthoamino formyl quinoleines, nouveaux synthons heterocycliques," J Heterocyclic Chem, 17(3):465-473 (1980).

Gole et al., "Plasma Proteins Modified by Tyrosine Nitration in Acute Respiratory Distress Syndrome," Am J Physiol Lung Cell Mol Physiol, 2000, vol. 278, pp. L961-L967.
Gomez, "Dimethyltin(IV) 2,6-disubstituted pyridine complexes," J. Organometallic Chemistry, 672(2):115-122 (2003).
Good, "Measuring field loss in children administered vigabatrin: a problem in search of a solution," J AAPOS. 15(5):411-2 (2011).
Gopalakrishnan et al., "Stable expression, pharmacologic properties and regulation of the human neuronal nicotinic acetylcholine alpha 4 beta 2 receptor," J. Pharmacol. Exp. Ther., 276:289-297 (1996).
Gould et al., "[3H]nitrendipine-labeled calcium channels discriminate inorganic calcium agonists and antagonists," Proc. Natl. Acad. Sci. U.S.A., 79:3656-3660 (1982).
Grandy et al., "Cloning of the cDNA and gene for a human D2 dopamine receptor," Proc. Natl. Acad. Sci. U.S.A., 86:9762-9766 (1989).
Green et al., "Characterization of [(3)H]-CGP54626A binding to heterodimeric GABA(B) receptors stably expressed in mammalian cells," Brit. J. Pharmacol., 131:1766-1774 (2000).
Green et al., "Influence of Various Agents on Corneal Permeability," American Journal of Ophthalmology, 1971; 72(5):897-905.
Grob et al., "Die Synthese von 5-Oxy-benz(cd)indolin and dessen Umpagerung in 5-Keto-1,3,4,5-tetrahydro-benz(cd)indol," Helvetica Chimica Acta, Verlag Helvetica Chimica Acta, CH, 33(6):1796-1808 (1950).
Gromachevskaya et al., "4H-3,1-benzoxazines. 2. Synthesis of 2,4-substituted 1 2-dihydro-4H-3,1-benzoxazines," Chemistry of Heterocyclic Compounds, 24(6):692-697 (Jun. 1988).
Grotto et al., "Importance of the lipid peroxidation biomarkers and methodological aspects for malondialdehyde quantification," Quim Nova, 2009; 32(1):169-174.
Halilovic et al., "ADX-103, a Novel Small Molecule Aldehyde Sequestering Agent, Decreases Retinal Edema and Inflammation in a Rat Model of Diabetic Macular Edema," ARVO Annual Meeting Abstract, 2 pages (Jul. 2018).
Hampson et al., "Cannabidiol and (-)Delta9-tetrahydrocannabinol are neuroprotective antioxidants," Proc. Nat. Acad. Sci 95:8268-8273 (1998).
Hassan et al., "Oxidative stress in systemic lupus erythematosus and rheumatoid arthritis patients: relationship to disease manifestations and activity," International Journal of Rheumatic Diseases, 14(1):325-331 (2011).
Herbort et al., "Endotoxin-induced uveitis in the rat," Graefe's Arch Clin Exp Ophthalmol, 1988; 226:553-8.
Hessen et al., "Dry Eye: an Inflammatory Ocular Disease," J Ophthalmic Vis Res, 2014; 9(2):240-250.
Heuillet et al., "Characterization of a Human NK1 Tachykinin Receptor in the Astrocytoma Cell Line U 373 Mg," J. Neurochem., 60:868-876 (1993).
Highlights of Prescribing Information, Bridion® (sugammadex) Injection, for intravenous use, Initial U.S. Approval: 2015, Last Revised Dec. 2015 (19 pages).
Hogema et al., "Pharmacologic rescue of lethal seizures in mice deficient in succinate semialdehyde dehydrogenase," Nat Genet. 29:212-16 (2001).
Hom et al., "Allergic conjunctivitis and dry eye syndrome," Ann Allergy Asthma Immunol, 2012; 108(3):163-6.
Hong et al., "Laboratory Scale Production of Injectable Liposomes By Using Cell Disruptor . . . ," Journal of Pharmaceutical Investigation, 2015, vol. 45, pp. 73-78.
Hope et al., "Characterization of a human 5-hydroxytryptamine3 receptor type A (h5-HT3R-AS) subunit stably expressed in HEK293 cells," Brit. J. Pharmacol., 118:1237-1245 (1996).
Horner et al., "Analogs of 3-Amino-7-chloro-1,2,4-benzotriazine 1-Oxide as Antimalarial Agents," J. Med. Chem., 11(5):946-949 (1968).
Hoyer et al., "Characterization of the 5-HT1B recognition site in rat brain: binding studies with (-)[125I]iodocyanopindolol," Eur. J. Pharmacol., 118:1-12 (1985).
Huang et al., "Characterization of Calcium Phosphate Nanoparticles Based on a PEGylated Chelator for Gene Delivery," ACS Appl Mater Interfaces, 9:10435?10445 (Mar. 2017).

(56) References Cited

OTHER PUBLICATIONS

Huang et al., "Identification of human Ether-a-go-go related gene modulators by three screening platforms in an academic drug-discovery setting," Assay Drug Dev Technol., 8(6):727-42 (2010).
Huang et al., "Novel peptide inhibitors of angiotensin-converting enzyme 2," J. Biol. Chem., 278:15532-15540 (2003).
Hubbard, "Geometrical Isomerization of Vitamin A, Retinene and Retinene Oxime," Journal of the American Chemical Society, 78(18):4662-4667 (1956).
Hugues et al., "Preparation of a pure monoiodo derivative of the bee venom neurotoxin apamin and its binding properties to rat brain synaptosomes," J. Biol. Chem., 257:2762-2769 (1982).
Hurd et al., "Reaction of Propiolactone with Aniline Derivatives," Journal of the American Chemical Society, 74(23):5889-5893 (1952).
Inoue et al., "Filter-binding assay procedure for thyroid hormone receptors," Anal Biochem. 134(1):176 (1983).
International Search Report issued in PCT/US2006/020320 dated Sep. 26, 2006 (10 pages).
International Search Report issued in PCT/US2010/059719 dated Feb. 8, 2011 (7 pages).
International Search Report issued in PCT/US2013/076592 dated Apr. 30, 2014 (10 pages).
International Search Report issued in PCT/US2014/012356 dated May 30, 2014 (11 pages).
International Search Report issued in PCT/US2014/012762 mailed by the U.S. Patent and Trademark Office dated Jul. 18, 2014.
International Search Report issued in PCT/US2016/048054 mailed by the U.S. Patent and Trademark Office dated Nov. 4, 2016.
International Search Report issued in PCT/US2016/048064 dated Nov. 15, 2016 (8 pages).
International Search Report issued in PCT/US2017/020020 dated May 24, 2017 (12 pages).
International Search Report issued in PCT/US2017/031808 mailed by the U.S. Patent and Trademark Office dated Aug. 11, 2017.
International Search Report issued in PCT/US2017/047958 dated Oct. 31, 2017 (10 pages).
International Search Report issued in PCT/US2018/023000 dated Jun. 1, 2018 (8 pages).
International Search Report issued in PCT/US2018/055310 dated Jan. 29, 2019 (9 pages).
International Search Report issued in PCT/US2019/041942 dated Sep. 30, 2019 (18 pages).
International Search Report issued in PCT/US2019/044929 dated Nov. 20, 2019 (15 pages).
International Search Report issued in PCT/US2019/045206 dated Oct. 17, 2019 (13 pages).
International Search Report issued in PCT/US2019/052961 dated Dec. 10, 2019 (11 pages).
International Search Report issued in PCT/US2019/054263 dated Jan. 6, 2020 (13 pages).
International Search Report issued in PCT/US2019/064669 dated Feb. 27, 2020 (12 pages).
International Search Report issued in PCT/US2020/024022, dated Jun. 17, 2020 (11 pages).
International Search Report issued in PCT/US2020/031138 mailed by the U.S. Patent and Trademark Office dated Jul. 13, 2020.
International Search Report issued in PCT/US2020/031219 dated Aug. 2020 (14 pages).
International Search Report issued in PCT/US2021/023884 mailed by the U.S. Patent and Trademark Office dated Jul. 28, 2021.
International Search Report issued in PCT/US2021/032335, mailed by the U.S. Patent and Trademark Office dated Jul. 27, 2021.
International Search Report issued in PCT/US2021/035948 mailed by the U.S. Patent and Trademark Office dated Oct. 26, 2021.
International Search Report issued in PCT/U.S. Pat. No. 2021027148 mailed by the U.S. Patent and Trademark Office dated Jun. 28, 2021.
International Search Report issued in PCT/US2022/035898 mailed by the U.S. Patent and Trademark Office dated Nov. 16, 2022.

Iriyama et al., "A2E, a pigment of the lipofuscin of retinal pigment epithelial cells, is an endogenous ligand for retinoic acid receptor," J Biol Chem., 283(18):11947-53 (2008) Epub Mar. 6, 2008.
Ishida et al., "Stabilization of calmodulin-dependent protein kinase II through the autoinhibitory domain," J. Biol. Chem., 270:2163-2170 (1995).
Ito et al., "A Medium-Term Rat Liver Bioassay for Rapid in vivo Detection of Carcinogenic Potential of Chemicals," Cancer Science, 94(1):3-8 (2003).
Itokawa et al., "Antiangiogenic effect by SU5416 is partly attributable to inhibition of Flt-1 receptor signaling," Mol. Cancer Ther., 1:295-302 (2002).
Janowski et al., "Structural requirements of ligands for the oxysterol liver X receptors LXRalpha and LXRbeta," Proc. Natl. Acad. Sci. USA, 96:266-271 (1999).
Joseph et al., "Binding of (-)-[3H]-CGP12177 at two sites in recombinant human beta 1-adrenoceptors and interaction with beta-blockers," Naun.-Sch. Arch. Pharm., 369:525-532 (2004).
Kam et al., "Topical Cyclodextrin Reduces Amyloid Beta and Inflammation Improving Retinal Function in Ageing Mice," Experimental Eye Research, 2015; 135:59-66.
Kamino et al., "Deficiency in mitochondrial aldehyde dehydrogenase increases the risk for late-onset Alzheimer's disease in the Japanese population," Biochemical and Biophysical Research Communications, 273(1):192-196 (2000).
Karahashi et al., "Changes of caspase activities involved in apoptosis of a macrophage-like cell line J774.1/JA-4 treated with lipopolysaccharide (LPS) and cycloheximide," Biol. Pharm. Bull., 23:140-144 (2000).
Karan et al., Lipofuscin Accumulation, Abnormal Electrophysiology, and Photoreceptor Degeneration in Mutant ELOVL4 Transgenic Mice: A Model for Macular Degeneration, Proc Natl Acad Sci USA, 102(11):4164-4169 (2005).
Katugampola et al., "[(125)I]-(Pyr(1))Apelin-13 is a novel radioligand for localizing the APJ orphan receptor in human and rat tissues with evidence for a vasoconstrictor role in man," Brit. J. Pharmacol., 132:1255-1260 (2001).
Kenney et al., "The Cascade Hypothesis of Keratoconus," Contact Lens & Eye, 26:139-146 (2003).
Keri, "Rosacea," Merck Manual, Professional Version, https://www.merckmanuals.com/professional/dermatologic-disorders/acne-and-related-disorders/rosacea, 7 pages (2017).
Knapp et al., "Intraocular Availability of Topically Applied Mycophenolate Mofetil in Rabbits," J. Ocul. Pharmacol. Ther., 2003; 19(2):181-192.
La Rosa et al., "Allergic conjunctivitis: a comprehensive review of the literature," Itai J Pediatr, 2013; 39:18.
Landor et al., "Allenes. Part 49, 4-Amino-2-(1-hydroxyalkyl)quinolones from Phenylhydroxylamine and Allenic Nitrites," J Chem Soc Perkin Trans 1, pp. 251-254 (1989).
Langin et al., "[3H]RX821002: a new tool for the identification of alpha 2A-adrenoceptors," Eur. J. Pharmacol., 167: 95-104 (1989).
Lankin et al., "Role of Oxidative Stress in the Genesis of Atherosclerosis and Diabetes Mellitus: A Personal Look Back on 50 Years of Research," Curr. Aging Sci. 10:18 (2017).
Le et al., "Ligand binding and functional properties of human angiotensin AT1 receptors in transiently and stably expressed CHO-K1 cells," Eur. J. Pharmacol., 513:35-45 (2005).
Lee et al., "Human recombinant soluble guanylyl cyclase: expression, purification, and regulation," Proc. Natl. Acad. Sci. USA, 97(20):10763-10768 (2000).
Lee et al., "The human brain cholecystokinin-B/gastrin receptor. Cloning and characterization," J. Biol. Chem., 268: 8164-8169 (1993).
Leibundgut et al., "Oxidation-specific epitopes and immunological responses: Translational biotheranostic implications for atherosclerosis," Current Opinion in Pharmacology, 13(2):168-179 (2013).
Leonardi et al., "Correlation Between Conjunctival Provocation Test (CPT) and Systemic Allergometric Tests in Allergic Conjunctivitis," Eye, 1990; 4:760-764.
Leonardi, "Allergy and allergic mediators in tears," Exp. Eye Res., 2013; 117:106-17.

(56) References Cited

OTHER PUBLICATIONS

Leurs et al., "Pharmacological characterization of the human histamine H2 receptor stably expressed in Chinese hamster ovary cells," Brit. J. Pharmacol., 112: 847-854 (1994).
Levin et al., "The myocardium-protective Gly-49 variant of the beta 1-adrenergic receptor exhibits constitutive activity and increased desensitization and down-regulation," J. Biol.Chem., 277:30429-30435 (2002).
Li et al., "Effect of Vitamin A Supplementation on Rhodopsin Mutants Threonine-17 -> Methionine and Proline-347 -> Serine in Transgenic Mice and in Cell Cultures," Proc Natl Acad Sci USA, 95(20):11933-11938 (1998).
Liang et al., "Ocular safety of cationic emulsion of cyclosporine in an in vitro corneal wound-healing model and an acute in vivo rabbit model," Mol Vis, 2012; 18:2195-204.
Liu et al., "Comparison of human, mouse, rat, and guinea pig histamine H4 receptors reveals substantial pharmacological species variation," J. Pharmacol. Exp. Ther., 299:121-130 (2001).
Loftsson et al., "Cyclodextrin Microparticles for Drug Delivery to the Posterior Segment of the Eye: Aqueous Dexamethasone Eye Drops," Journal of Pharmacy and Pharmacology, 2007; 59(5):629-635.
Loftsson et al., "Cyclodextrins in Eye Drop Formulations: Enhanced Topical Delivery of Corticosteroids to the Eye," Acta Ophthalmologica Scandinavica, 2002; 80(2):144-150.
Lopachin et al., "Molecular mechanisms of aldehyde toxicity: a chemical perspective," Chem Res Toxicol, 2014; 27(7):1081-91.
Lovenberg et al., "Cloning and functional expression of the human histamine H3 receptor," Mol. Pharmacol., 55:1101-1107 (1999).
Lukas, R.J., "Characterization of curaremimetic neurotoxin binding sites on membrane fractions derived from the human medulloblastoma clonal line, T15671," J. Neurochem., 46:1936-1941 (1986).
Luthin et al., "Characterization of two affinity states of adenosine A2a receptors with a new radioligand, 2-[2-(4-amino-3-[125I]iodophenyl)ethylamino]adenosine," Mol. Pharmacol., 47:307-313 (1995).
MacDonald et al., "ADX-102, a novel aldehyde trap, reduces nociceptive behavior in mouse models of carrageenan and CFA induced pain," Int'l Conference on Pain Research & Management Abstract, J Pain Relief, 5 (5 Suppl):50 (Oct. 2016).
MacDonald et al., "Inhibition of fibroblast activation to the myofibroblast phenotype in neonatal rat cardiac fibroblasts using a small molecule aldehyde trap," ASCB Annual Meeting Abstract, p. 2 (Dec. 2016).
MacDonald et al., "Molecular characterization of the melanin-concentrating hormone/receptor complex: identification of critical residues involved in binding and activation," Mol. Pharmacol., 58:217-225 (2000).
Maeda et al., "Involvement of All-trans-retinal in Acute Light-induced Retinopathy of Mice," J Biol Chem, 284(22):15173-83 (May 2009).
Maeda et al., "Primary amines protect against retinal degeneration in mouse models of retinopathies," Nat Chem Biol, 2011; 8(2):170-178.
Mantey et al., "Discovery of a high affinity radioligand for the human orphan receptor, bombesin receptor subtype 3, which demonstrates that it has a unique pharmacology compared with other mammalian bombesin receptors," J. Biol. Chem., 272:26062-26071 (1997).
Marnett, "Oxy radicals, lipid peroxidation and DNA damage," Toxicology, 181-182:219-222 (2002).
Martin et al., "Molecular cloning and functional characterization of murine cysteinyl-leukotriene 1 (CysLT(1)) receptors.," Biochem. Pharmacol., 62:1193-1200 (2001).
Matern et al., "Seizures in a boy with succinic semialdehyde dehydrogenase deficiency treated with vigabatrin (gamma-vinyl-GABA)," J Inherit Metab Dis., 19(3):313-8 (1996).
Mathew et al., "Updates in the management of diabetic macular edema," J Diabetes Res. 2015; 2015:794036.
Maurice et al., "Advances in targeting cyclic nucleotide phosphodiesterases," Nat Rev Drug Discov., 2014; 13:290-314.

McCord et al., "Superoxide dismutase. An enzymic function for erythrocuprein (hemocuprein).," J. Biol. Chem., 1969; 244: 6049-6055.
McGinnity et al., "Evaluation of fresh and cryopreserved hepatocytes as in vitro drug metabolism tools for the prediction of metabolic clearance." Drug Metab. Dispos., 32(11):1247-1253 (2004).
McLaurin et al., "Phase 3 Randomized Double-Masked Study of Efficacy and Safety of Once-Daily 0.77% Olopatadine Hydrochloride Ophthalmic Solution in Subjects with Allergic Conjunctivitis Using the Conjunctival Allergen Challenge Model," Clinical Science, 2015; 34(10):1245-1251.
Medline Plus. Macular Degeneration—age-related. (6 pages) (2013).
Meijer et al., "Biochemical and cellular effects of roscovitine, a potent and selective inhibitor of the cyclin-dependent kinases cdc2, cdk2 and cdk5," Eur. J. Biochem., 243:527-536 (1997).
Meng et al., "Cloning and pharmacological characterization of a rat kappa opioid receptor," Proc. Natl. Acad. Sci. U.S.A., 90:9954-9958 (1993).
Merck Sharp & Dohme Corp., "Bridion® (sugammadex) Injection Prescribing Information, for intravenous use," Highlights of Prescribing Information. 2015.
Mialet et al., "Isolation of the serotoninergic 5-HT4(e) receptor from human heart and comparative analysis of its pharmacological profile in C6-glial and CHO cell lines," Brit. J. Pharmacol., 129:771-781 (2000).
Miceli et al., "Efficacy of keratinocyte growth factor-2 in dextran sulfate sodium-induced murine colitis," J Pharmacol Exp Ther, 290(1):464-71 (Jul. 1999).
Mishra et al., "Recent Patents and Emerging Therapeutics in the Treatment of Allergic Conjunctivitis," Recent Pat. Inflamm. Allergy Drug Discov.; 2011; 5(1):26-36.
Mittl et al., "Structure of recombinant human CPP32 in complex with the tetrapeptide acetyl-Asp-Val-Ala-Asp fluoromethyl ketone," J. Biol. Chem., 272:6539-6547 (1997).
Monaghan et al., "The distribution of [3H]kainic acid binding sites in rat CNS as determined by autoradiography," Brain Res., 252:91-100 (1982).
Monsma et al., "Cloning and expression of a novel serotonin receptor with high affinity for tricyclic psychotropic drugs," Mol. Pharmacol., 43:320-327 (1993).
Mulheron et al., "Human 5-HT1A receptor expressed in insect cells activates endogenous G(o)-like G protein(s)," J. Biol. Chem., 269:12954-12962 (1994).
Muller-Enoch et al., "[6.7-Dihydroxycoumarin (Aesculetin) as a substrate for catechol-o-methyltransferase (author's transl)]," Z. Naturforsch., 31:280-284 (1976).
Munro et al., "Molecular characterization of a peripheral receptor for cannabinoids," Nature, 365:61-65 (1993).
Murphy et al., "Characterization of quisqualate recognition sites in rat brain tissue using DL-[3H]alpha-amino-3-hydroxy-5-methylisoxazole-4-propionic acid (AMPA) and a filtration assay," Neurochem. Res., 12:775-781 (1987).
Nagai et al., Improved corneal toxicity and permeability of tranilast by the preparation of ophthalmic formulations containing its nanoparticles, J Oleo Sci, 2014; 63(2):177-86.
Nagase et al., "Design and characterization of a fluorogenic substrate selectively hydrolyzed by stromelysin 1 (matrix metalloproteinase-3),"J. Biol. Chem., 269:20952-20957 (1994).
Nakamura et al., "Involvement of Oxidative Stress on Corneal Epithelial Alterations in a Blink-Suppressed Dry Eye," Investigative Ophthalmology and Visual Science, 2007; 48(4):1552-1558.
Negre-Salvayre et al., "Advanced Lipid Peroxidation End Products in Oxidative Damage to Proteins. Potential Role in Diseases and Therapeutic Prospects for the Inhibitors," Br J Pharmacol, 2008; 153(1):6-20.
Nema et al., "Excipients and Their Use in injectable Products," PDA J Pharm Sci Technol, 51(4):166-171 (1997).
Nerurkar et al., "13-Aryl-Glutaconic Acids. II. Imides of Certain 13-aryl-Glutaconic and Glutaric Acids," J Org Chem, 24(12):2055-2056 (1959).
Nerurkar et al., "Beta-Arylglutaconic Acids. II. Imides of Certain Beta-Arylglutaconic and Glutaric Acids," J Org Chem, 24(12):2055-2056 (1959).

(56) References Cited

OTHER PUBLICATIONS

Nielsen and Bundgaard, "Glycolamide esters as biolabile prodrugs of carboxylic acid agents: synthesis, stability, bioconversion, and physicochemical properties," J Pharm Sci. 1988;77(4):285-98.
Niwa et al., "Protein oxidative damage in the stratum corneum: Evidence for a link between environmental oxidants and the changing prevalence and nature of atopic dermatitis in Japan," Br J Dermatol., 2003; 149:248.
Nociari et al., "Beta cyclodextrins bind, stabilize, and remove lipofuscin bisretinoids from retinal pigment epithelium," Proc Natl Acad Sci U.S.A., 2014; E1402-E1408.
Noorwez et al., "Pharmacological Chaperone-mediated in Vivo Folding and Stablization ofthe P23H-Opsin Mutant Associated with Autosomal Dominant Retinitis Pigmentosa," J Biol Chem, 278:14442-14450 (2003).
O'Brien et al., "Aldehyde Sources, Metabolism, Molecular Toxicity Mechanisms, and Possible Effects on Human Health," Crit Rev Toxicol, 2005; 35:609-662.
Obourn et al., "Hormone- and DNA-binding mechanisms of the recombinant human estrogen receptor," Biochemistry 32(24):6229 (1993).
Organisciak et al., "Susceptibility to Retinal Light Damage in Transgenic Rats with Rhodopsin Mutations," Invest Ophthalmol Vis Sci, 44(2):486-492 (2003).
Ousler et al., "Use of the Controlled Adverse Environment (CAE) in Clinical Research: A Review," Opthalmology and Therapy, Sep. 27, 2017, vol. 6, pp. 263-276.
Pacholczyk et al., "Expression cloning of a cocaine- and antidepressant-sensitive human noradrenaline transporter," Nature, 350:350-354 (1991).
Pal et al., "Sulfur mustard analog induces oxidative stress and activates signaling cascades in the skin of SKH-1 hairless mice," Free Radic Biol Med., 47(11):1640-51 (2009).
Palchaudhuri et al., "Corticotropin-releasing factor receptor type 1 from Tupaia belangeri-cloning, functional expression and tissue distribution," Eur. J. Biochem., 258:78-84 (1998).
Parish et al., "Isolation and One-Step Preparation of A2E and iso-A2E, Fluorophores from Human Retinal Pigment Epithelium," Proc Natl Acad Sci USA, 95(25):14609-14613 (1998).
Park et al., "Homogeneous proximity tyrosine kinase assays: scintillation proximity assay versus homogeneous time-resolved fluorescence," Anal. Biochem., 269:94-104 (1999).
Parracho et al., "Differences between the gut microflora of children with autistic spectrum disorders and that of healthy children," Journal of Medical Microbiology, 54:987-991 (2005).
Patel C.Y., "Subtype selectivity of peptide analogs for all five cloned human somatostatin receptors (hsstr 1-5)," Endocrinology, 135:2814-2817 (1994).
Pearl et al., "Inherited disorders of gamma-aminobutyric acid metabolism and advances in ALDH5A1 mutation identification," Dev Med Child Neurol., 57(7):611-617 (2015).
Pellock, "Balancing clinical benefits of vigabatrin with its associated risk of vision loss," Acta Neurologica. Scandinavica. Supplementum., 124(s192):83-91 (2011).
Peralta et al., "Distinct primary structures, ligand-binding properties and tissue-specific expression of four human muscarinic acetylcholine receptors," EMBO. J., 6:3923-3929 (1987).
Petroski et al., "Selective labeling of embryonic neurons cultured on astrocyte monolayers with 5(6)-carboxyfluorescein diacetate (CFDA)," Journal of Neuroscience Methods, 52(1):23-32 (1994).
Pfaar et al., "Perspectives in allergen immunotherapy: 2017 and beyond," Allergy, 2018; 73(Suppl 104):5-23.
Pickering, D.S., "Pharmacological characterization of melatonin binding sites in Syrian hamster hypothalamus," Eur. J. Pharmacol., 175:71-77 (1990).
Pontikis et al., "Cyclodextrin alleviates neuronal storage of cholesterol in Niemann-Pick C disease without evidence of detectable blood-brain barrier permeability," Journal of Inherited Metabolic Disease, 2013; 36(3):491-498.
Pozzi et al., "Modification of Collagen IV by Glucose or Methylglyoxal Alters Distinct Mesangial Cell Function," Journal of the American Society of Nephrology, 20:2119-2125 (2009).
Pruneau et al., "LF 16.0335, a novel potent and selective nonpeptide antagonist of the human bradykinin B2 receptor," Brit. J. Pharmacol., 125:365-372 (1998).
Radu et al., "Treatment with Isotretinoin Inhibits Lipofuscin Accumulation in a Mouse Model of Recessive Stargardt's Macular Degeneration," Proc Natl Acad Sci USA, 100(8):4742-4747(2003).
Rapp et al., "The Effects of Local Anaesthetics on Retinal Function," Vision Res, 22(9):1097-1103 (1982).
Rauli et al., "Validation of Malondialdehyde and 4-Hydroxy-2-trans-Nonenal Measurement in Plasma by NICI-GC-MS1," J Biochem., 1998; 123:918-923.
Rizzo, "The role of fatty aldehyde dehydrogenase in epidermal structure and function" Dermato-Endocrinol, 3(2):91-99 (2011).
Roat, "Allergic Conjunctivitis," Merck Manual Professional Version, 3 pages (2016), Available at: https://www.merckmanuals.com/professional/eye-disorders/conjunctival-and-scleral-disorders/allergic-conjunctivitis.
Roat, "Keratoconjunctivitis Sicca," Merck Manual Professional Version, 5 pages (2016), Available at: https://www.merckmanuals.com/professional/eye-disorders/corneal-disorders/keratoconjunctivitis-sicca.
Roat, "Ocular Mucous Membrane Pemphigoid," Merck Manual Professional Version, 3 pages (2016), Available at: https://www.merckmanuals.com/professional/eye-disorders/conjunctival-and-scleral-disorders/ocular-mucous-membrane-pemphigoid.
Roat, "Scleritis," Merck Manual Professional Version, 3 pages (2016), Available at: https://www.merckmanuals.com/professional/eye-disorders/conjunctival-and-scleral-disorders/scleritis.
Roberts et al., "Basic Principles of Organic Chemistry," 2nd edition, copyright 1977 W. A. Benjamin, Inc., pp. 580-582.
Roberts et al., "Experimental Organic Chemistry—A Miniscale Approach," copyright 1994 by Saunders College Publishing, pp. 580-581 and 584-586.
Rohrer et al., "Cloning and characterization of a fourth human somatostatin receptor," Proc. Natl. Acad. Sci. U.S.A., 90:4196-4200 (1993).
Roumen et al., "Serum Lipofuscin as a Prognostic Indicator of Adult Respiratory Distress Syndrome and Multiple Organ Failure," British Journal of Surgery, 1994, vol. 81, pp. 1300-1305.
Rønborg et al., "Exposure chamber for allergen challenge. The development and validation of a new concept," Allergy, 1996; 51(2):82-8.
Sahi et al., "Hepatocytes as a tool in drug metabolism, transport and safety evaluations in drug discovery." Current Drug Discov. Technol., 7(3):188-198 (2010).
Salvatore et al., "Molecular cloning and characterization ofthe human A3 adenosine receptor," Proc. Natl. Acad. Sci. U.S.A., 90:10365-10369 (1993).
Samsonov et al., "Impact of Atherosclerosis- and Diabetes-Related Dicarbonyls on Vascular Endothelial Permeability: A Comparative Assessment," Oxid. Med. Cell Longev. Article 1625130 (2017).
Sanchez et al., "Allergic Conjunctivitis," J Investig Allergol Clin Immunol., 2011; 21(2): 1-19.
Sandikci et al., "Lipid Peroxidation and Antioxidant Defence System in Patients with Active or Inactive Behcet's Disease," Acta Derm Venereol, 2003; 83:342-346.
Sarafian et al., "Synergistic cytotoxicity of Delta(9)-tetrahydrocannabinol and butylated hydroxyanisole," Toxicology Letters, 133(2-3):171-179 (2002).
Sarup et al., "Resolution of high and low affinity progesterone receptors from human breast carcinoma T47D cells," J. Biol. Chem., 263:5624-5633 (1988).
Sasaki et al., "Retinal drug delivery using eyedrop preparations of poly-L-lysine-modified liposomes," Eur J Pharm Biopharm, 2013; 83(3):364-9.
Satici et al., "Malondialdehyde and antioxidant enzyme levels in the aqueous humor of rabbits in endotoxin-induced uveitis," Eur J Ophthalmol, 2003; 13(9-10):779-83.

(56) References Cited

OTHER PUBLICATIONS

Sayed et al., "Metabolic Activation of R,S-1-(Tetrahydro-2-turanyl)-5-fluorouracil (Ftorafur) to 5-fluorouracil by Soluble Enzymes," Cancer Research, 43:4039-4044 (1983).
Schaumberg et al., "Epidemiology of dry eye syndrome," Lacrimal Gland, Tear Film, and Dry Eye Syndromes 3, Kluwer Academic/Plenum Publishers, pp. 989-998 (2002).
Schaumberg et al., "Prevalence of Dry Eye Disease among US Men: Estimates from the Physicians' Health Studies," Arch Ophthalmol, 2009; 127(6):763-768.
Schioth et al., "Characterization of the binding of MSH-B, HB-228, GHRP-6 and 153N-6 to the human melanocortin receptor subtypes," Neuropeptides, 31:565-571 (1997).
Schramm et al., "The Cross-linked Biopolymer Hyaluronic Acid as an Artificial Vitreous Substitute," Invest Ophthalmol Vis Sci, 53(2):613-621 (Feb. 2012).
Schwinn et al., "Molecular cloning and expression of the cDNA for a novel alpha 1-adrenergic receptor subtype," J. Biol. Chem., 265:8183-8189 (1990).
Sciuto et al., "Therapeutic Treatments of Phosgene-Induced Lung Injury," Inhal Toxicol, 16(8):565-580 (2004).
Search Report and Written Opinion issued by the Intellectual Property Office of Singapore for Singapore Patent Application No. 11201504859Y dated Aug. 1, 2016 (12 pages).
Serbecic et al., "Anti-oxidative vitamins prevent lipid-peroxidation and apoptosis in corneal endothelial cells," Cell Tissue Res, 320(3):465-75 (Jun. 2005).
SG Search Report and Written Opinion from 11201505587Y, dated Jul. 12, 2016.
Shank et al., "Ion and temperature effects on the binding of gamma-aminobutyrate to its receptors and the high-affinity transport system," J. Neurochem., 54:2007-2015 (1990).
Shen et al., "Molecular cloning and expression of a 5-hydroxytryptamine7 serotonin receptor subtype," J. Biol. Chem., 268:18200-18204 (1993).
Sheppard et al., "Targeting Anterior Uveitis: A Focus on Iontophoresis . . . ", Sep. 1, 2018, Retrieved from Internet URL: https://www.nyee.edu/files/NYEE/Health%20Professionals/Continuing%20Medical%20Education/Enduring%20CME%20Activities/158_supplement.small_v1_FINAL%20082818.pdf.
Sherman et al., "Cellular Defenses Against Unfolded Proteins: A Cell Biologist Thinks about Neurodegenerative Diseases," Neuron, 29(1):15-32 (2001).
Sieving et al., "Inhibition of the Visual Cycle in vivo by 13-cis Retinoic Acid Protects from Light Damage and Provides a Mechanism for Night Blindness in Isotretinoin Therapy," Proc Natl Acad Sci USA, 98(4):1835-1840 (2001).
Snead et al., "Gamma-hydroxybutyric acid," New England Journal of Medicine, 352(26):2721-2732 (2005).
Snell et al., "Novel structure having antagonist actions at both the glycine site of the N-Methyl-D-Aspartate receptor and neuronal voltage-sensitive sodium channels. Biochemical, electrophysiological, and behavioral characterization," J Pharmacol Exp Ther, 292(1):215-227 (2000).
Spagnol et al., "Efficient synthesis of tricyclic benzobisoxazines by silica gel catalysis," J Org Chem, 2;72(5):1867-1869 (Mar. 2007).
Sparrow et al. "Phospholipid meets all-trans-retinal: the making of RPE bisretinoids," Journal of Lipid Research, 51: 247-261 (2010).
Sus et al., "Uber die Lichtreaktion der o-Chinondiazide V Mitteilungl) Ubergange heterocyclischer 6-Ringe in heterocyclische 5-Ringe," Liebigs Ann. Chem. 583:150 (1953).
Tang-Liu et al., "Effects of four penetration enhancers on corneal permeability of drugs in vitro," Journal of Pharmaceutical Sciences, 1994; 83(1):85-90.
Tatsumi et al., "Pharmacological profile of neuroleptics at human monoamine transporters," Eur. J. Pharmacol., 368: 277-283 (1999).
Tian et al., "First total synthesis and determination of the absolute configuration of 1-N-methyl-3-methylamino- [N-butanoicacid-3-(9-methyl-8-propen-7-one)-amide]—benzo [f][1,7]naphthyridine-2-one, a novel benzonaphthyridine alkaloid," Tetrahedron Letters, 53:4892-4895 (2012).
Turk et al., "Serum anti-carbonic anhydrase antibodies and oxidant-antioxidant balance in patients with acute anterior uveitis," Ocul Immunol Inflamm, 22(2):127-32 (Apr. 2014).
Ueda et al., "Evaluation of a Sulfobutyl Ether 13-Cyclodextrin as a Solubilizing/Stabilizing Agent for Several Drugs," Drug Dev Ind Pharm, 24(9):863-867(1998).
Upadhyaya et al., "The sphingolipid degradation product trans-2-hexadecenal forms adducts with DNA," Biochem Biophy Res Comm., 424(1):18-21 (2012).
U.S. Appl. No. 16/157,069, filed Oct. 10, 2018.
U.S. Appl. No. 16/168,309, filed Oct. 23, 2018.
U.S. Appl. No. 16/262,364, filed Jan. 30, 2019.
U.S. Appl. No. 16/277,865, filed Feb. 15, 2019.
U.S. Appl. No. 16/300,020, filed Nov. 8, 2018.
U.S. Appl. No. 16/374,845, filed Apr. 4, 2019.
U.S. Appl. No. 16/530,705, filed Aug. 3, 2019.
U.S. Appl. No. 16/547,930, filed Aug. 22, 2019.
U.S. Appl. No. 16/582,720, filed Sep. 25, 2019.
U.S. Appl. No. 16/592,572, filed Oct. 3, 2019.
Vanachayangkul et al., "Inhibition of heme peroxidases by melamine," Enzyme Research, 2012:416062 (2012).
Vignon et al., "[3H]thienyl-phencyclidine ([3H]TCP) binds to two different sites in rat brain. Localization by autoradiographic and biochemical techniques," Brain Res., 378:133-141 (1986).
Vlaskina et al., "Novel Synthesis of Substituted Benzimidazoles by Reduction of Esters of 4-Alkylamino-3,5-dinitrobenzoic Acids by Tin Chloride," Chemistry of Heterocyclic Compounds, vol. 40(4):523-524 (2004).
Vogel et al., "Thirty years beyond discovery-clinical trials in succinic semialdehyde dehydrogenase deficiency, a disorder of GABA metabolism," J Inherit Metab Dis., 36(3):401-10 (2013).
Voziyan et al., "A Post-Amadori Inhibitor Pyridoxamine also Inhibits Chemical Modification of Proteins by Scavenging Carbonyl Intermediates for Carbohydrate and Lipid Degradation," J Biol Chem, 277(5):3397-3403 (2002).
Wagner et al., "Omega-conotoxin GVIA binding to a high-affinity receptor in brain: characterization, calcium sensitivity, and solubilization," J. Neurosci., 8:3354-3359 (1988).
Wakamatsu et al., "Evaluation of lipid oxidative stress status and inflammation in atopic ocular surface disease," Mol Vis, 16:2465-75 (Nov. 2010).
Wall et al., "Plant Antitumor Agents. 30. Synthesis and Structure Activity of Novel Camptothecin Analogs," J. Med. Chem., 36(18):2689-2700 (1993).
Walter et al., "Novel Complex N-Heterocycles via Intramolecular 1,5-Electrocyclizations: 1,2,3,4,4a,5,5a,10-Octahydropyrido-[4",3":2',3']cyclobuta[1',2':4,5]pyrrolo[2,3-b]pyridines," Heterocycles, 48(8):1581-1591 (1998).
Wang et al., "A facile one-pot synthesis of 2-substituted-3-aminoquinolines: Preparation of benzo[b]naphthyridine-3-carbonitriles," Tetrahedron, 60(13):2937-2942 (2004).
Wang et al., "Human mu opiate receptor. cDNA and genomic clones, pharmacologic characterization and chromosomal assignment," FEBS Lett., 338:217-222 (1994).
Wang et al., "Markers of oxidative and nitrosative stress in systemic lupus erythematosus: correlation with disease activity," Arthritis and Rheumatism, 62(7):2064-2072 (2010).
Wang, X.K., "Pharmacological study on recombinant human GABA-A receptor complex containing alphas (leucine 155 to valine) combined with beta3gamma2s subunits," Acta. Pharmacol. Sin., 22:521-523 (2001).
Waslidge et al., "A colorimetric method for the determination of lipoxygenase activity suitable for use in a high throughput assay format," Anal. Biochem., 231:354-358 (1995).
Weaver et al., "The Th17 pathway and inflammatory diseases of the intestines, lungs, and skin," Annu. Rev. Pathol., 8:477-512 (2013).
Webb et al., "Intralesional cytokines in chronic oxazolone-induced contact sensitivity suggest roles for tumor necrosis factor alpha and interleukin-4," J Invest Dermatol, 111(1):86-92 (Jul. 1998).

(56) References Cited

OTHER PUBLICATIONS

Weishaar et al., "Multiple molecular forms of cyclic nucleotide phosphodiesterase in cardiac and smooth muscle and in platelets. Isolation, characterization, and effects of various reference phosphodiesterase inhibitors and cardiotonic agents," Biochem. Pharmacol., 35:787-800 (1986).

Weng et al., "Insights into the Function of Rim Protein in Photoreceptors and Etiology of Stargardt's Disease from the Phenotype in abcr Knockout Mice," Cell, 98(1):13-23 (1999).

Westphal et al., "Reactions with Pryridinium Pyruvic Acid Esters," Pharmazie, 31(11)770-773 (1976) [English Translation].

Wieland et al., "Subtype selectivity and antagonistic profile of the nonpeptide Y1 receptor antagonist BIBP 3226," J. Pharmacol. Exp. Ther., 275:143-149 (1995).

Witt-Enderby et al., "Characterization and regulation of the human ML1A melatonin receptor stably expressed in Chinese hamster ovary cells," Mol. Pharmacol., 50:166-174 (1996).

Wolkenberg et al., "Design, synthesis, and evaluation of novel 3,6-diaryl-4-aminoalkoxyquinolines as selective agonists of somatostatin receptor subtype 2," J Med Chem, 54(7):2351-2358 (2011).

Wood et al., "Aldehyde Load in Ischemia-Reperfusion Brain Injury: Neuroprotection by Neutralization of reactive Aldehydes with Phenelzine," Brain Res, 1122(1):184-190 (2006).

Wood et al., "The concept of "aldehyde load" in neurodegenerative mechanisms: cytotoxicity of the polyamine degradation products hydrogen peroxide, acrolein, 3-aminopropanal, 3-acetamidiorioanal and 4-aminobutanal in a retinal ganglion cell line," Brain Research, 1145:150-156 (2007).

Wurch et al., "Sequence and functional analysis of cloned guinea pig and rat serotonin 5-HT1D receptors: common pharmacological features within the 5-HT1D receptor subfamily," J. Neurochem., 68:410-418 (1997).

Yadav et al., "Regulation of NF-kB-lnduced Inflammatory Signaling by Lipid Peroxidation-Derived Aldehydes," Oxidative Med & Cell Longev, 2013, Art ID 690545, 11 pages (2013).

Yarnell, "Light Flips the Lipid Switch: Palmitoylation—the reversible attachment of palmitate to proteins—gets a new role in vision," C&EN, 82(29):22-23 (2004).

Yokomizo et al., "Hydroxyeicosanoids bind to and activate the low affinity leukotriene B4 receptor, BLT2," J. Biol. Chem., 276:12454-12459 (2001).

Zagol-Ikapitte et al., "Characterization of scavengers of y-ketoaldehydes that do not inhibit prostaglandin biosynthesis," Chem Res Toxicol, 23(1):240-250 (2010).

Zhang et al., "Potent nonsteroidal progesterone receptor agonists: synthesis and SAR study of 6-aryl benzoxazines," Bioorg Med Chem Lett, 12(5):787-90 (Mar. 2002).

Zhou et al., "Chemical and biological evidence for base propenals as the major source ofthe endogenous M1dG adduct in cellular DNA," J Biol Chem., 280(27):25377-82 (2005).

Zhou et al., "Cloning and expression of human and rat D1 dopamine receptors," Nature, 347:76-80 (1990).

Zhou et al., "Mechanisms for the induction of HNE- MDA- and AGE-adducts, RAGE and VEGF in retinal pigment epithelial cells," Exp Eye Res., 80(4):567-80 (2005).

COMPOSITIONS AND METHODS OF TREATING RETINAL DISEASE

CROSS-REFERENCE TO RELATED APPLICATIONS

This application is a continuation of U.S. patent application Ser. No. 16/241,851, filed Jan. 7, 2019, which is a continuation of U.S. patent application Ser. No. 15/861,332, filed Jan. 3, 2018, issued as U.S. Pat. No. 10,202,348, which is a continuation of U.S. patent application Ser. No. 15/488,205, filed Apr. 14, 2017, issued as U.S. Pat. No. 9,896,419, which is a continuation of U.S. patent application Ser. No. 15/049,890, filed Feb. 22, 2016, issued as U.S. Pat. No. 9,650,342, which is a continuation of U.S. patent application Ser. No. 14/581,462, filed Dec. 23, 2014, issued as U.S. Pat. No. 9,265,759, which is a continuation of U.S. patent application Ser. No. 13/175,218, filed Jul. 1, 2011, issued as U.S. Pat. No. 8,940,721, which is a continuation of U.S. patent application Ser. No. 11/441,848, filed May 26, 2006, issued as U.S. Pat. No. 7,973,025, which claims the benefit of U.S. Provisional Application No. 60/723,577, filed Oct. 4, 2005, and U.S. Provisional Application No. 60/685,460, filed May 26, 2005. The entire contents of each cited priority application are incorporated by reference herein.

FIELD OF THE INVENTION

This application relates to compositions and methods for treating macular degeneration and other forms of retinal disease whose etiology involves the accumulation of A2E and/or lipofuscin in retinal tissue, more specifically, for preventing the accumulation of A2E.

BACKGROUND OF THE INVENTION

Two forms of retinal disease include Stargardt disease, which afflicts young adults, and age related macular degeneration (AMD), which afflicts adults in midlife and later. Both forms are characterized by the progressive degeneration of cone photoreceptors located in the foveal region of the macula, which degeneration leads to loss of high acuity vision in the central visual field. The disease has been associated with the accumulation of toxic biochemicals, including lipofuscin, inside retinal pigment epithelium (RPE) cells and extracellular drusen where the RPE cells are in contact with Bruch's membrane. The accumulation of these retinotoxic mixtures is one of the most important known risk factors in the etiology of AMD.

AMD begins as a "dry form" without vascular complications. Currently there are no known treatments for dry form AMD. One patient in ten progresses to a late-stage form of the disease known as "wet form" AMD which is characterized by choroidal neovascularization that invades the macula and disrupts retinal and RPE tissue. Most current wet form AMD treatments suppress vascular growth or inflammatory processes.

During the normal visual cycle (summarized in FIG. 1), most trans-RAL is sequestered by opsin proteins in photoreceptor outer segment disc membranes. This sequestering mechanism protects the trans-RAL group from reacting with phosphatidylethanolamine (PE) before trans-RAL dehydrogenase (RDH) converts trans-RAL to the alcohol trans-retinol. Some trans-RAL molecules escape sequestering, however, and react with phosphatidylethanolamine to form first N-retinylidene-phosphatidylethanolamine (APE) and then N-retinylidene-N-retinyl-phosphatidylethanolamine (A2PE) in the discs of photoreceptor outer segments. Both A2PE and trans-RAL that has escaped sequestering are transported out of photoreceptor disc membranes by an ATP-binding cassette transporter called Rim protein (RmP) or ABCA4 (formerly ABCR). Following this transportation, trans-RAL is reduced to trans-retinol by RDH and crosses the outer-segment (OS) plasma membrane into the extracellular space where it is taken up by cells of the retinal pigment epithelium (RPE).

A2PE is taken up by RPE cell lysosomes when RPE cells ingest photoreceptor outer segments that are shed routinely. Once inside the lysosomes, A2PE is converted irreversibly to A2E, which causes lysosomal failure. Lysosomal failure poisons the RPE cells and compromises their ability to provide biochemical support to retinal photoreceptors, leading to the progressive degeneration of both cell types.

Multiple factors affect the rate of A2E accumulation, both genetic and environmental. For example, a hereditary mutation in both copies of the ABCA4 transporter gene increases the accumulation of A2E and leads to Stargardt disease in children and young adults. A later onset form of Stargardt disease is associated with ABCA4 mutations that are more benign. Stargardt disease is thought by many to be an early onset form of AMD, where the normal age-related accumulation of A2E is accelerated by the ABCA4 mutation to a sufficient extent that the disease is triggered decades before AMD normally appears.

With respect to environmental factors, it is well established in animal models that the rate of A2E formation varies with light exposure. It has been shown that a fatty acid (phosphatidylglycerol) can protect RPE cells from A2E induced cell death, and that other dietary factors can influence disease progression, including zinc (which affects retinol oxidoreductase activity).

There is a need for effective treatments of dry form AMD and Stargardt disease which arrest disease progression and preserve or restore vision.

SUMMARY OF THE INVENTION

The invention relates to compositions and methods for treating macular degeneration and other forms of retinal disease whose etiology involves the accumulation of A2E and/or lipofuscin in retinal tissue.

In one embodiment, the present invention provides compositions and methods for treating macular degeneration and other retinal disease with an etiology involving the accumulation of A2E and/or lipofuscin by limiting the formation of cytotoxic A2E. For example, A2E formation is prevented or reduced by limiting the amount of unsequestered trans-RAL available for reaction with phosphatidyl ethanolamine (PE) in photoreceptor outer segments. In one approach, a therapeutic compound, i.e., an "RAL-trap" is administered to a patient, whereby the drug competes with PE for trans-RAL by forming a Schiff base adduct. "Free RAL" is defined as RAL that is not bound to a visual cycle protein.

In another embodiment, the invention relates to a method of identifying a drug to treat macular degeneration and other forms of retinal disease whose etiology involves the accumulation of A2E and/or lipofuscin may include administering a candidate agent to a subject having, or at risk for developing, macular degeneration and retinal disease, and measuring A2E formation in the presence of the candidate agent, relative to A2E formation in the absence of the candidate agent.

A wide variety of drugs are contemplated for use in the methods of the invention. In some embodiments, inhibitors of A2E formation include RAL-traps. For example, the pharmacological target of such RAL-trap compounds is trans-RAL which has escaped sequestering by opsins in photoreceptor outer segments. RAL-traps include, for example, cyclic amines and five- and six-membered heterocyclic amines which may have one or more pairs of conjugated double bonds, and, for example, may be aromatic. In some embodiments, the RAL trap is administered to a subject as a topical formulation for delivery by eye drops or via skin patch.

The invention relates to a method of treating or preventing macular degeneration and other forms of retinal disease whose etiology involves the accumulation of A2E and/or lipofuscin in a subject, the method by administering a composition that reduces the level of A2E accumulation relative to the level of A2E accumulation in the subject without administration of the composition. The invention also relates to a method of treating or preventing macular degeneration and other forms of retinal disease whose etiology involves the accumulation of A2E and/or lipofuscin in a subject by administering to the subject a composition that reduces the level of A2E formation relative to the level of A2E formation in the subject without administration of the composition.

In some embodiments, the methods of the invention further include diagnosing macular degeneration and other forms of retinal disease whose etiology involves the accumulation of A2E and/or lipofuscin in the subject. In other embodiments, the methods further include monitoring the macular degeneration and other forms of retinal disease whose etiology involves the accumulation of A2E and/or lipofuscin in the subject.

In one aspect, the invention relates to administering a composition that includes a compound selected from benzocaine, procaine, orthocaine, tricaine (MS222, compound 6), and methyl anthranilate.

In one aspect, the methods of the invention include administering a composition that includes a compound of the formula IV:

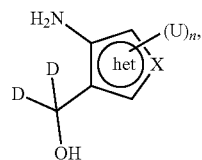

where $X^1$ is O, N(H), or S, het is a 5 or 6-membered heterocycle, n is 0, 1, 2, or 3, and each D is an unbranched lower alkyl group. Each D can be the same or different. In one embodiment, the Ds are the same.

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In one embodiment each D is methyl.

In some embodiments, the substituents (U) are selected such that the first $pK_a$ of the ring $NH_2$ is approximately 3.5.

In one aspect, the methods of the invention include administering a composition that includes a compound of formula I.

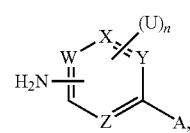

where, W, X, Y, and Z are each, independently, N, S, O, CU or CH, and at least one of W, X, Y, and Z is N; n is 0, 1, 2, 3, or 4, A is

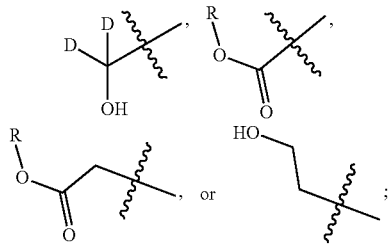

D is unbranched lower alkyl; R is substituted or unsubstituted C1, C2, C3, C4, C5, C6, C7, or C8, straight chain alkyl, or substituted or unsubstituted C3, C4, C5, C6, C7, or C8, branched chain alkyl.

U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In one embodiment, the identity of W, X, Y, and Z are such that the compound comprises a pyridine, pyridazine, pyrazine, or pyrimidine ring.

In some embodiments, U is aryl. For example, U can be benzene. U can also be a halo-substituted benzene.

In some embodiments, A is

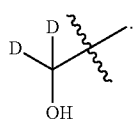

In some embodiments, A is

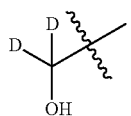

and D is methyl.

In some embodiments, two adjacent U substituents are connected to form a 5- or 6-membered optionally substituted ring. For example, the substituents can be connected to form a benzene ring, forming a compound having the structure according to formula Ia:

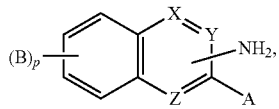

Ia where X, Y, and Z are each, independently, N, O, S, CH, or absent, such that at least one of X, Y, and Z is N; p is 0, 1, 2, or 3, B is a halogen atom, hydroxyl, carbamoyl, substituted or unsubstituted aryl or amino, A is

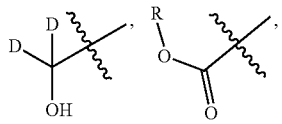

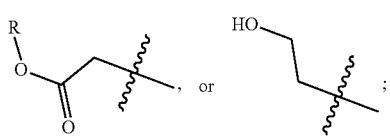

D is unbranched lower alkyl, and R is substituted or unsubstituted C1, C2, C3, C4, C5, C6, C7, or C8 straight chain alkyl, or substituted or unsubstituted C3, C4, C5, C6, C7 or C8 branched chain alkyl.

Compounds of Formula 1 can include:

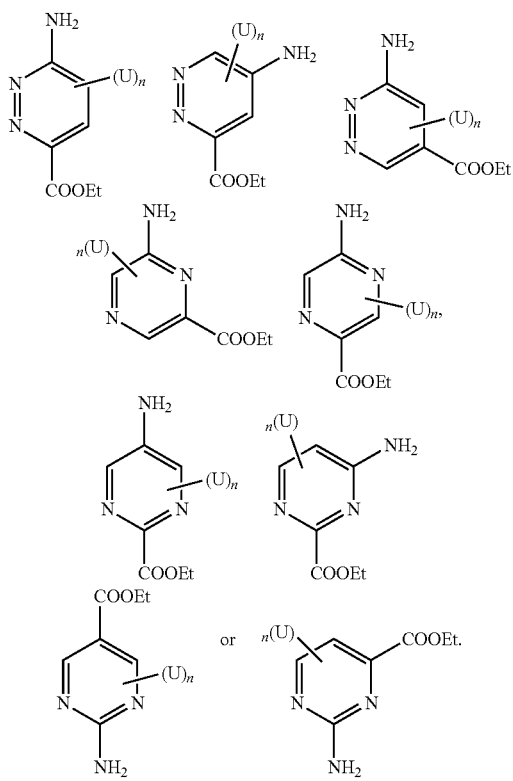

In one embodiment, the composition used in the methods of the invention includes the compound

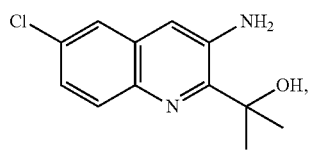 [SMILES: CC(C)(O)c1nc2ccc(Cl)cc2cc1N]

or a pharmaceutically acceptable salt thereof.

In one aspect, the methods of the invention include administering a composition that includes a compound of formula II or IIa:

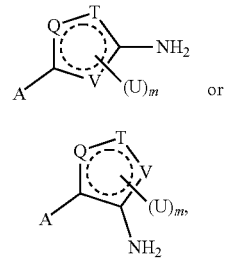

II or

IIa where Q, T, and V are each, independently, N or NH, S, O, CU or CH, such that at least one of Q, T and V is not CU or CH; the dashed ring represents two double bonds within the ring, which comply with the valency requirements of the atoms and heteroatoms present in the ring; m is 0, 1, or 2; A is

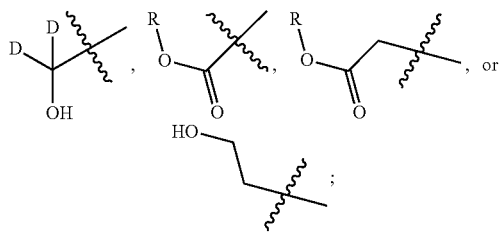

D is unbranched lower alkyl; R is substituted or unsubstituted C1, C2, C3, C4, C5, C6, C7 or C8 straight chain alkyl, or substituted or unsubstituted C3, C4, C5, C6, C7 or C8 branched chain alkyl.

U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In one embodiment, in compounds of formula II or IIa, U is aryl. For example, U can be benzene. U can also be a halo-substituted benzene ring.

In some embodiments, in compounds of formula II or IIa, A is

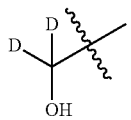

In some compounds, each D is methyl.

In one embodiment, in compounds of formula II or IIa, Q, T, and V are selected such that the composition includes a furan or thiophene ring.

In one embodiment, in compounds of formula II or IIa, U is lower alkyl. For example, U can be methyl.

In one embodiment, in compounds of formula II or IIa, U is a halogen atom. For example, U can be fluoro or chloro.

One example of a composition useful in the methods of the invention includes the compound

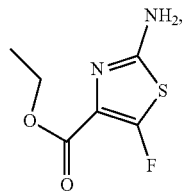

or a pharmaceutically acceptable salt thereof.

In one aspect, the methods of the invention include administering a composition that includes a compound of formula III:

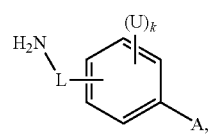

III where, L is a bond or $CH_2$; A is

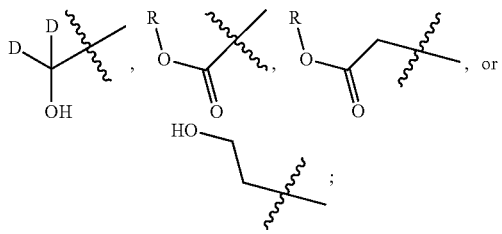

D is unbranched lower alkyl; R is substituted or unsubstituted C1, C2, C3, C4, C5, C6, C7 or C8 straight chain alkyl, or substituted or unsubstituted C3, C4, C5, C6, C7 or C8 branched chain alkyl, and k is 0, 1, 2, 3, or 4.

U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In some embodiments, in compounds of formula III, A is

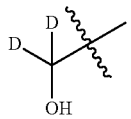

In some compounds, each D is methyl.

In some embodiments, in compounds of formula III, U is aryl. For example, U can be benzene. In some embodiments, U is a halo-substituted benzene ring.

In one aspect, the methods of the invention include administering a composition that includes a compound of formula III, wherein two adjacent U substituents are connected to form a 5- or 6-membered, optionally substituted ring.

For example, methods of the invention include administering a composition that includes a compound of formula III, where adjacent U substituents are connected as a heterocyclic ring, forming a compound having the structure according to formula IIIa:

IIIa

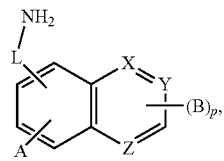

wherein L is a single bond or $CH_2$,

X, Y, and Z are each, independently, N, NH, O, S, CB, CH, or absent, such that at least one of X, Y, and Z is N or NH; p is 0, 1, 2, or 3; B is a halogen atom, hydroxyl, carbamoyl, aryl or amino; A is

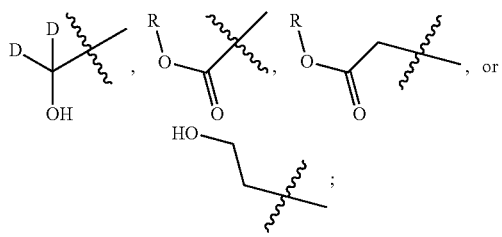

D is unbranched lower alkyl; and R is substituted or unsubstituted C1, C2, C3, C4, C5, C6, C7, or C8 straight chain alkyl, or substituted or unsubstituted C3, C4, C5, C6, C7 or C8 branched chain alkyl.

In one embodiment, in the compound of formula IIIa, the fused heterocyclic ring is a 6-membered ring. For example, the ring can be a pyridine ring.

In one embodiment, in the compound of formula IIIa, the fused heterocyclic ring is a 5-membered ring. For example, the ring can be thiazole, oxazole, or imidazole.

In one embodiment, in the compound of formula IIIa, B is aryl. For example, B is benzene.

In one embodiment, methods of the invention include administering a composition that includes a compound selected from

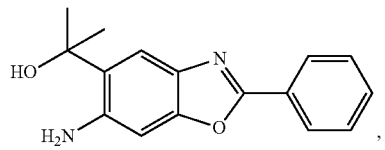

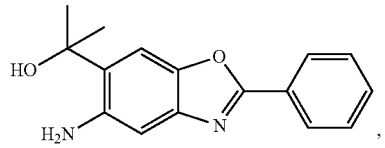

or pharmaceutically acceptable salts thereof.

In one aspect, methods of the invention include administering a composition chronically to treat or prevent macular degeneration and other forms of retinal disease whose etiology involves the accumulation of A2E and/or lipofuscin.

In one aspect, the invention also relates to a method of identifying a drug for treating or preventing macular degeneration and other forms of retinal disease whose etiology involves the accumulation of A2E and/or lipofuscin, by administering a candidate drug to a subject having, or who is at risk for developing, macular degeneration or other forms of retinal disease whose etiology involves the accumulation of A2E and/or lipofuscin; and measuring accumulation of A2E in the subject; where reduced accumulation of A2E in the presence of the candidate drug relative to accumulation of A2E in the absence of the candidate drug indicates that the candidate drug is a drug for treating or preventing macular degeneration and other forms of retinal disease whose etiology involves the accumulation of A2E and/or lipofuscin.

In another aspect, the invention relates to a method of identifying a drug for treating or preventing macular degeneration and other forms of retinal disease whose etiology involves the accumulation of A2E and/or lipofuscin, by: contacting an in-vitro model of the visual cycle with the candidate drug; and measuring accumulation of A2E; wherein reduced accumulation of A2E in the presence of the candidate drug relative to accumulation of A2E in the absence of the candidate drug indicates that the candidate drug is a drug for treating or preventing macular degeneration and other forms of retinal disease whose etiology involves the accumulation of A2E and/or lipofuscin.

The present invention relates to compounds and their use to treat macular degeneration, including dry form AMD and Stargardt disease, and other forms of retinal disease whose etiology involves the accumulation of A2E and/or lipofuscin. One aspect of the invention includes a compound of formula I, Ia, II, IIa, III, IIIa, or IV wherein a Schiff Base adduct of said compound and 11-cis-RAL possesses an extinction coefficient equal to or less than that of free 11-cis-RAL. In one embodiment, the absorbance peak of the Schiff Base adduct is at a wavelength equal to or lower than that of free 11-cis-RAL.

Another aspect of the invention includes a compound having the formula IV:

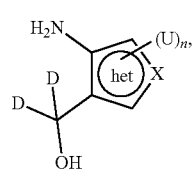

wherein X is O, N(H), or S and het is a 5 or 6-membered heterocycle. n represents 0, 1, 2, or 3, and each D is an unbranched lower alkyl group. U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more heteroatoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. In another embodiment, each D is methyl. In another embodiment, the $pK_a$ of the ring $NH_2$ ($NH_2 \rightarrow NH$) is approximately 3.5.

Another aspect of the invention includes a compound represented by general formula I:

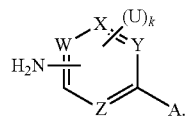

W, X, Y, and Z are each, independently, N, S, O, CU or CH, such that at least one of W, X, Y, and Z is N. A is

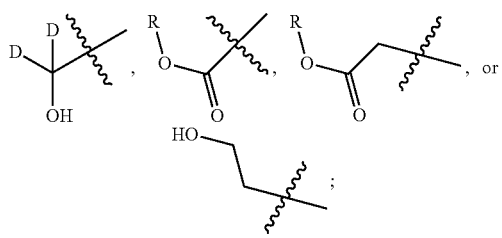

D is unbranched lower alkyl. R is substituted or unsubstituted C1, C2, C3, C4, C5, C6, C7, or C8, straight chain alkyl, or substituted or unsubstituted C3, C4, C5, C6, C7, or C8, branched chain alkyl. U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more heteroatoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. n represents 0, 1, 2, 3, or 4. In one embodiment, the compound comprises a pyridine, pyridazine, pyrazine, or pyrimidine ring. In another embodiment, U is an aryl. In another embodiment, U is a benzene. In another embodiment, U is a halo-substituted benzene. In one embodiment, A is

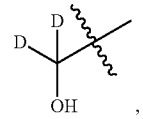

and D is methyl. In another embodiment, two adjacent U substituents are connected to form a 5- or 6-membered optionally substituted ring. In another embodiment, two adjacent U substituents are connected as a benzene ring, forming a compound having the structure according to formula Ia:

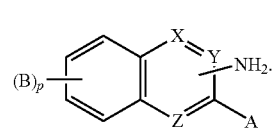

X, Y, and Z are each, independently, N, O, S, C(H), or absent, such that at least one of X, Y, and Z is N. p is 0, 1, 2, or 3. B is a halogen atom, hydroxyl, carbamoyl, aryl or amino. A is

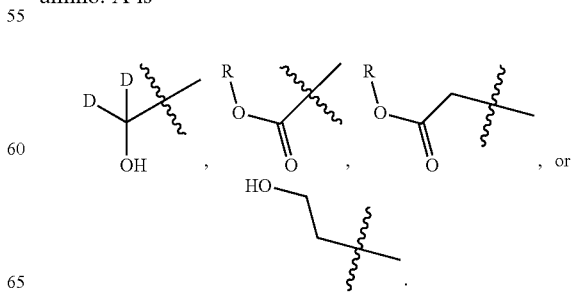

D is unbranched lower alkyl, and R is substituted or unsubstituted C1, C2, C3, C4, C5, C6, C7, or C8 straight chain alkyl, or substituted or unsubstituted C3, C4, C5, C6, C7, or C8 branched chain alkyl.

In one embodiment, the composition comprises a compound selected from:

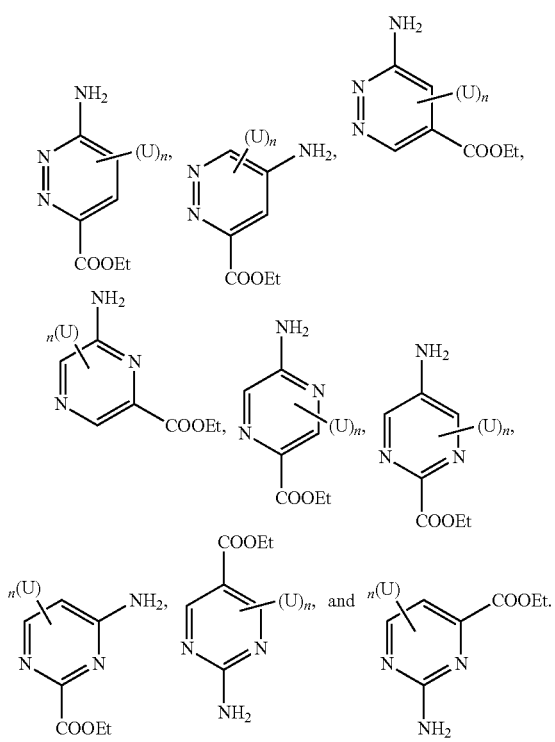

In a further embodiment, the compound is selected from

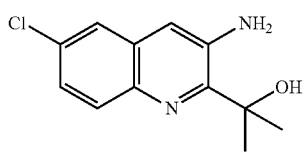 [SMILES: CC(C)(O)c1nc2ccc(Cl)cc2cc1N]

and pharmaceutically acceptable salts thereof.

Another aspect of the invention includes a compound represented by formula II or IIa:

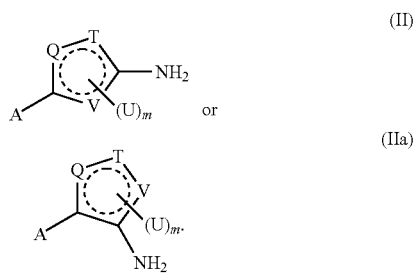

Q, T, and V are each, independently, N(H), S, O, CU or CH, such that at least one of Q, T and V is not CU or CH. The dashed ring represents two double bonds within the ring, which comply with the valency requirements of the atoms and heteroatoms present in the ring. m is 0, 1, or 2. A is

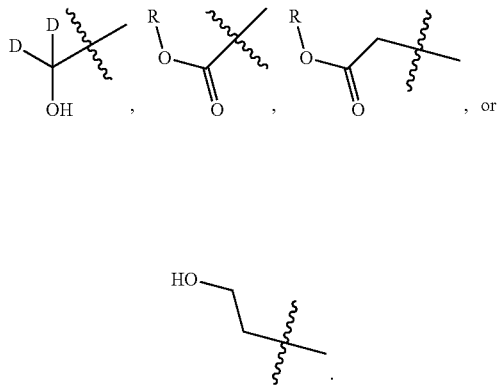

D is unbranched lower alkyl. R is substituted or unsubstituted C1, C2, C3, C4, C5, C6, C7 or C8 straight chain alkyl, or substituted or unsubstituted C3, C4, C5, C6, C7, or C8 branched chain alkyl. U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more heteroatoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. In one embodiment, U is an aryl. In another embodiment, U is a benzene. In another embodiment, U is a halo-substituted benzene. In one embodiment, A is

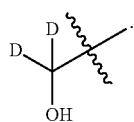

In another embodiment, each D is methyl. In another embodiment, Q, T, and V are selected such that the composition comprises a furan or thiophene ring. In another embodiment, U is lower alkyl. In another embodiment, U is methyl. In another embodiment, U is halogen atom. In another embodiment, U is fluoro. In a further embodiment, the compound is selected from

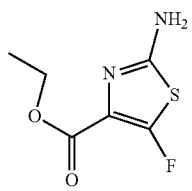

and pharmaceutically acceptable salts thereof.

Another aspect of the invention includes a compound represented by general formula III:

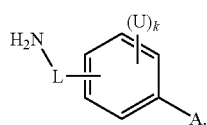
(III)

L is a single bond or CH$_2$. A is

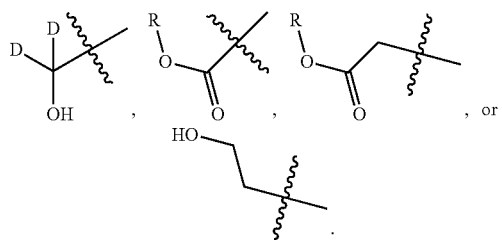
, or

D is unbranched lower alkyl. R is substituted or unsubstituted C1, C2, C3, C4, C5, C6, C7, or C8 straight chain alkyl, or substituted or unsubstituted C3, C4, C5, C6, C7, or C8 branched chain alkyl. U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. k is 0, 1, 2, 3, or 4. In one embodiment, A is

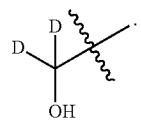

In another embodiment, each D is methyl. In another embodiment, U is an aryl. In another embodiment, U is a benzene. In another embodiment, U is a halo-substituted benzene. In another embodiment, two adjacent U substituents are connected to form a 5- or 6-membered optionally substituted ring. In another embodiment, two adjacent U substituents are connected as a heterocyclic ring, forming a compound having the structure according to formula IIIa:

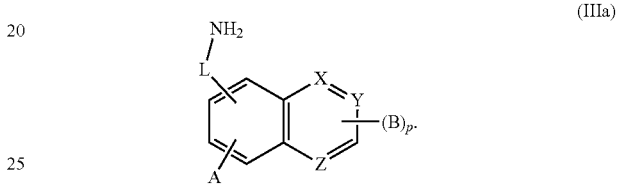
(IIIa)

X, Y, and Z are each, independently, N, O, S, CB, CH, or absent, such that at least one of X, Y, and Z is N. p is 0, 1, 2, or 3. B is a halogen atom, hydroxyl, carbamoyl, aryl or amino. A is

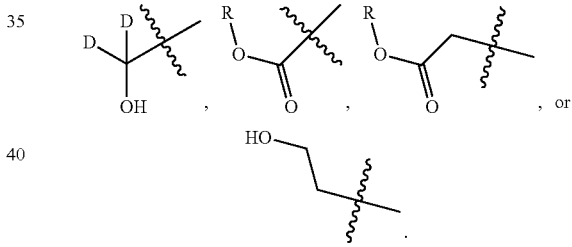
, or

D is unbranched lower alkyl. R is substituted or unsubstituted C1, C2, C3, C4, C5, C6, C7, or C8 straight chain alkyl, or substituted or unsubstituted C3, C4, C5, C6, C7, or C8 branched chain alkyl. In one embodiment, the fused heterocyclic ring is a 6-membered ring. In another embodiment, the fused heterocyclic ring is a pyridine ring. In another embodiment, the fused heterocyclic ring is a 5-membered ring. In another embodiment, the fused heterocyclic ring is selected from thiazole, oxazole, and imidazole. In another embodiment, B is aryl. In another embodiment, B is a benzene. In another embodiment, the compound is selected from

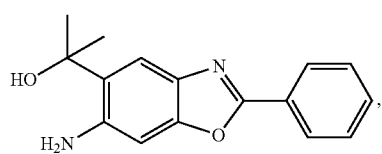
,

-continued

[chemical structure]

and pharmaceutically acceptable salts thereof.

Pharmaceutical compositions that include a compound of Formula I, Ia, II, IIa, III, IIIa, or IV or a pharmaceutically acceptable salt thereof are used in the methods of the invention. In one embodiment, the compound of Formula I, Ia, II, IIa, III, IIIa, or IV or a pharmaceutically acceptable salt thereof is co-administered with one or more additional therapies.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the examples.

DETAILED DESCRIPTION OF THE INVENTION

The present application provides compositions and methods for treating macular degeneration and other forms of retinal disease whose etiology involves the accumulation of A2E and/or lipofuscin, for example, by limiting the formation of cytotoxic A2E. A2E formation can be prevented or reduced by limiting the amount of trans RAL available for reaction with phosphatidyl ethanolamine (PE). Progressive A2E accumulation in RPE cells causes dry AMD. By reducing the amount of A2E accumulation, the present invention prevents the onset and/or progression of dry AMD. In one approach, a small molecule drug is administered that competes with PE for reaction with trans-RAL which has escaped sequestering by opsins in photoreceptor outer segments.

Figure 2:
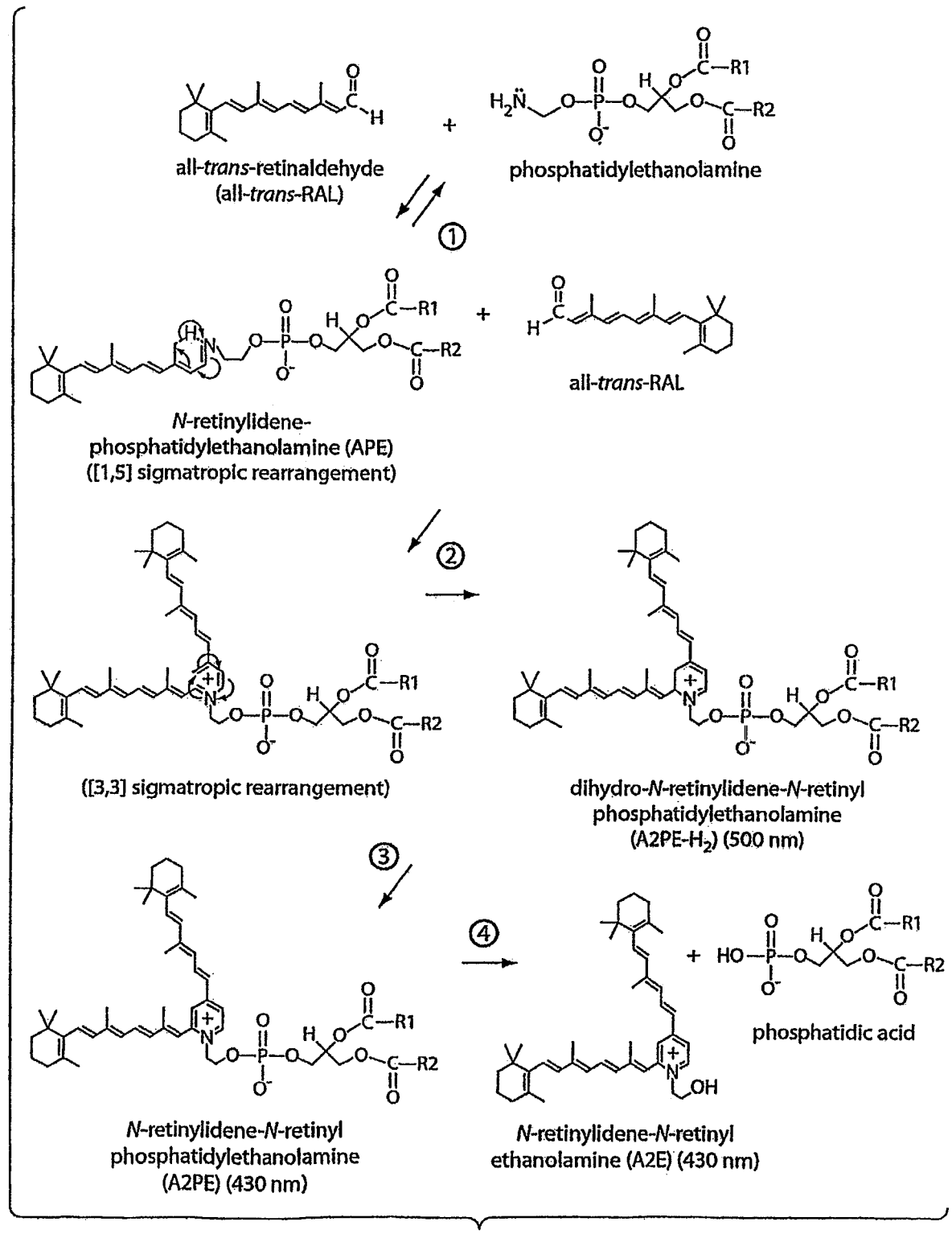
FIG. 2 is a schematic of the reaction pathway of A2E formation.

As shown in FIG. 2, RAL contains an aldehyde group. The aldehyde group stabilizes the binding of 11-cis-RAL to a photoreceptor membrane protein called opsin, by forming a Schiff base (FIG. 3) with an amino acid sidechain in the opsin binding site. Opsin releases trans-RAL from this binding site after transducing the photo-isomerization of bound 11-cis-RAL through a second messenger pathway.

While the aldehyde group on RAL is a useful molecular anchor for opsin binding, it is otherwise hazardous because of its Schiff base reactivity with other biological amines. To mitigate this risk, visual cycle proteins have evolved molecular mechanisms to continuously sequester RAL molecules, and thereby shield the aldehyde group from chemical side reactions. However, these protein sequestering mechanisms are not completely reliable. Over time, as much as one trans-RAL molecule in three escapes protein sequestering, where it is free to initiate a reaction cascade which begins with the formation of A2PE in photoreceptor outer segments and culminates in the formation of A2E in RPE cell lysosymes.

Once it is formed inside RPE cell lysosomes, A2E inhibits the ATP-driven proton pump in lysosome membranes and causes lysosomal pH to increase. The pH increase deactivates acid hydrolases and thereby causes lysosomal failure. Lysosomal failure is also caused the detergent action of A2E, which solubilizes lysosomal membranes. Lysosomal failure poisons the RPE cells and compromises their ability to provide biochemical support to retinal photoreceptors, leading to the progressive degeneration of both cell types and visual deterioration.

Hydroxyl amine and aromatic amine compounds were described as aldehyde nucleophiles in Schiff base reactions with RAL by Hubbard in 1956. Hubbard, *J. Am. Chem. Soc.* 78:4662, 1956; see also Rapp and Basinger, *Vision Res.* 22:1097, 1982, and Fowler et al., *J. Photochem. Photobiol. B* 8:183, 1991. Two such compounds which have a history of safe human use for other purposes include methyl anthranilate, a natural product found in grapes, and MS-222, a fish anesthetic used by fish breeders who are exposed to it occupationally during fish handling. However, MS-222 is pharmacologically active in the human retina and has no anesthetic activity in mammals.

In 1963, Dowling showed that anesthetics slow rhodopsin regeneration and dark adaptation in rats. This was the first report that such small molecules could modulate retinal visual performance. Dowling, *J. Gen. Physiol.* 46:1287, 1963. In 1982, Rapp & Basinger showed that certain local anesthetics form Schiff bases with RAL and slow dark adaptation in frogs. This was the first elucidation of the chemical reaction mechanism by which these compounds modulate retinal visual performance. Rapp and Basinger, *Vision Res.* 22:1097, 1982. In 1997, Bernstein et al. showed that MS222 (6) attenuates night vision reversibly in human occupational exposure. This was the first report that one such compound can be absorbed by the skin and modulate human retinal vision reversibly with no known side effects. Bernstein et al., *Am. J. Opthalmol.* 124:843, 1997.

Definitions

For convenience, before further description of exemplary embodiments, certain terms employed in the specification, examples, and appended claims are collected here.

These definitions should be read in light of the remainder of the disclosure and as understood by a person of skill in the art.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

In the present specification, the structural formula of the compound represents a certain isomer for convenience in some cases, but the present invention includes all isomers such as geometrical isomer, optical isomer based on an asymmetrical carbon, stereoisomer, tautomer and the like which occur structurally and an isomer mixture and is not limited to the description of the formula for convenience, and may be any one of isomer or a mixture. Therefore, an asymmetrical carbon atom may be present in the molecule and an optically active compound and a racemic compound may be present in the present compound, but the present invention is not limited to them and includes any one. In addition, a crystal polymorphism may be present but is not limiting, but any crystal form may be single or a crystal form mixture, or an anhydride or hydrate. Further, so-called metabolite which is produced by degradation of the present compound in vivo is included in the scope of the present invention.

It will be noted that the structure of some of the compounds of the invention include asymmetric (chiral) carbon atoms. It is to be understood accordingly that the isomers arising from such asymmetry are included within the scope of the invention, unless indicated otherwise. Such isomers can be obtained in substantially pure form by classical separation techniques and by stereochemically controlled synthesis. The compounds of this invention may exist in stereoisomeric form, therefore can be produced as individual stereoisomers or as mixtures.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J., Chem. Educ.* 1964, 41, 116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Further, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Tautomers" refers to compounds whose structures differ markedly in arrangement of atoms, but which exist in easy and rapid equilibrium. It is to be understood that compounds of Formula I may be depicted as different tautomers. It should also be understood that when compounds have tautomeric forms, all tautomeric forms are intended to be within the scope of the invention, and the naming of the compounds does not exclude any tautomer form.

Some compounds of the present invention can exist in a tautomeric form which are also intended to be encompassed within the scope of the present invention.

The compounds, salts and prodrugs of the present invention can exist in several tautomeric forms, including the enol and imine form, and the keto and enamine form and geometric isomers and mixtures thereof. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism, is exhibited by glucose. It arises as a result of the aldehyde group (—CHO) in a sugar chain molecule reacting with one of the hydroxy groups (—OH) in the same molecule to give it a cyclic (ring-shaped) form.

Tautomerizations are catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

Common tautomeric pairs are: ketone-enol, amide-nitrile, lactam-lactim, amide-imidic acid tautomerism in heterocyclic rings (e.g., in the nucleobases guanine, thymine, and cytosine), amine-enamine and enamine-enamine. Examples include:

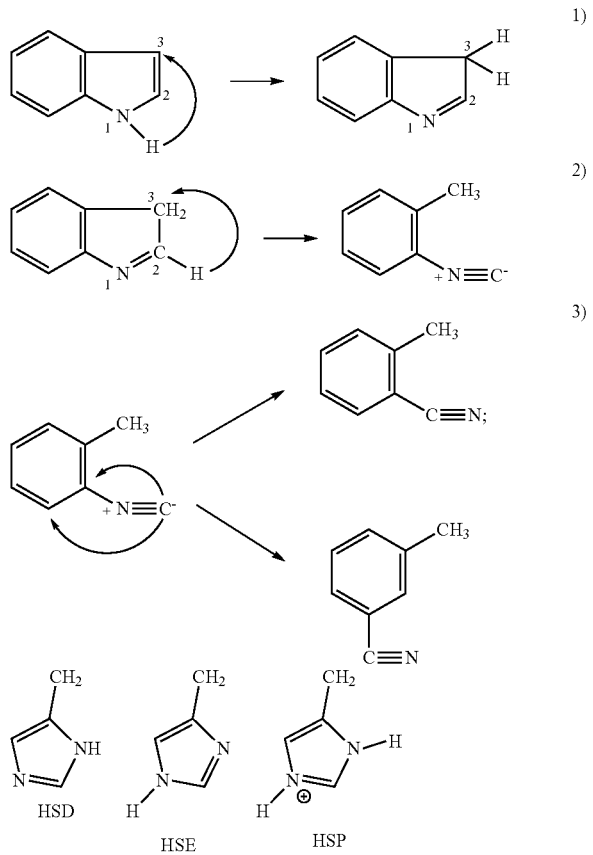

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative", refers to compounds that have a common core structure, and are substituted with various groups as described herein. For example, all of the compounds represented by formula I are indole derivatives, and have formula I as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject which may be predisposed to the disease, disorder and/or condition but has not yet been diagnosed as having it. Preventing a condition related to a disease includes stopping the condition from occurring after the disease has been diagnosed but before the condition has been diagnosed.

A "pharmaceutical composition" is a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the invention are capable of further forming salts. All of these forms are also contemplated within the scope of the claimed invention.

"Pharmaceutically acceptable salt" of a compound means a salt that is pharmaceutically acceptable and that possesses the desired pharmacological activity of the parent compound.

For example, the salt can be an acid addition salt. One embodiment of an acid addition salt is a hydrochloride salt The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed. (Mack Publishing Company, 1990). For example, salts can include, but are not limited to, the hydrochloride and acetate salts of the aliphatic amine-containing, hydroxyl amine-containing, and imine-containing compounds of the present invention.

It should be understood that all references to pharmaceutically acceptable salts include solvent addition forms (solvates) or crystal forms (polymorphs) as defined herein, of the same salt.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like. See Bundegaard, H. "Design of Prodrugs" p 1-92, Elsevier, New York-Oxford (1985).

"Protecting group" refers to a grouping of atoms that when attached to a reactive group in a molecule masks, reduces or prevents that reactivity. Examples of protecting groups can be found in Green and Wuts, *Protective Groups in Organic Chemistry*, (Wiley, $2^{nd}$ ed. 1991); Harrison and Harrison et al., *Compendium of Synthetic Organic Methods*, Vols. 1-8 (John Wiley and Sons, 1971-1996); and Kocienski, *Protecting Groups*, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butdyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Other suitable amine protecting groups are straightforwardly identified by those of skill in the art.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

The term "pharmaceutically acceptable salts" is art-recognized, and includes relatively non-toxic, inorganic and organic acid addition salts of compositions, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine; (trihydroxymethyl)aminoethane; and the like. See, for example, *J. Pharm. Sci.* 66:1-19 T1977.

A "patient," "subject," or "host" to be treated by the subject method may mean either a human or non-human animal, such as primates, mammals, and vertebrates.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition, such as macular degeneration or other forms of retinal disease whose etiology involves the accumulation of A2E and/or lipofuscin. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" is an art-recognized term. In certain embodiments, the term refers to an amount of a therapeutic agent that, when incorporated into a polymer, produces some desired effect at a reasonable benefit/risk ratio applicable to any medical treatment. In certain embodiments, the term refers to that amount necessary or sufficient to eliminate, reduce or maintain (e.g., prevent the spread of) a tumor or other target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug which produces 50% of its maximum response or effect, or alternatively, the dose which produces a pre-determined response in 50% of test subjects or preparations. The term "LD50" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "substituted," as used herein, means that any one or more hydrogens on the designated atom is replaced with a selection from the indicated group, provided that the designated atom's normal valency is not exceeded, and that the substitution results in a stable compound. When the substituent is keto (i.e., =O), then 2 hydrogens on the atom are replaced. Ring double bonds, as used herein, are double bonds that are formed between two adjacent ring atoms (e.g., C=C, C=N, or N=N).

With respect to any chemical compounds, the present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The chemical compounds described herein can have asymmetric centers. Compounds of the present invention containing an asymmetrically substituted atom can be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are, where appropriate, considered to be part of the present invention. All tautomers of shown or described compounds are also, where appropriate, considered to be part of the present invention.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

As used herein, "halo" or "halogen" refers to fluoro, chloro, bromo, and iodo. "Counterion" is used to represent a small, negatively charged species such as fluoride, chloride, bromide, iodide, hydroxide, acetate, and sulfate.

"Stable compound" and "stable structure" are meant to indicate a compound that is sufficiently robust to survive isolation, and as appropriate, purification from a reaction mixture, and formulation into an efficacious therapeutic agent.

"Free compound" is used herein to describe a compound in the unbound state.

"Extinction coefficient" is a constant used in the Beer-Lambert Law which relates the concentration of the substance being measured (in moles) to the absorbance of the substance in solution (how well the substance in solution blocks light beamed through it from getting out on the other side). It is an indicator of how much light a compound absorbs at a particular wavelength.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

"Small molecule" is an art-recognized term. In certain embodiments, this term refers to a molecule which has a molecular weight of less than about 2000 amu, or less than about 1000 amu, and even less than about 500 amu.

All percentages and ratios used herein, unless otherwise indicated, are by weight.

The "retina" is a region of the central nervous system with approximately 150 million neurons. It is located at the back of the eye where it rests upon a specialized epithelial tissue called retinal pigment epithelium or RPE. The retina initiates the first stage of visual processing by transducing visual stimuli in specialized neurons called "photoreceptors". Their synaptic outputs are processed by elaborate neural networks in the retina and then transmitted to the brain. The retina has evolved two specialized classes of photoreceptors to operate under a wide range of light conditions. "Rod" photoreceptors transduce visual images under low light conditions and mediate achromatic vision. "Cone" photoreceptors transduce visual images in dim to bright light conditions and mediate both color vision and high acuity vision.

Every photoreceptor is compartmentalized into two regions called the "outer" and "inner" segment. The inner segment is the neuronal cell body containing the cell nucleus. The inner segment survives for a lifetime in the absence of retinal disease. The outer segment is the region where the light sensitive visual pigment molecules are concentrated in a dense array of stacked membrane structures. Part of the outer segment is routinely shed and regrown in a diurnal process called outer segment renewal. Shed outer segments are ingested and metabolized by RPE cells.

The "macula" is the central region of the retina which contains the fovea where visual images are processed by long slender cones in high spatial detail ("visual acuity"). "Macular degeneration" is a form of retinal neurodegeneration which attacks the macula and destroys high acuity vision in the center of the visual field. AMD begins in a "dry form" characterized by residual lysosomal granules called lipofuscin in RPE cells, and by extracellular deposits called "drusen". Drusen contain cellular waste products excreted by RPE cells. "Lipofuscin" and drusen can be detected clinically by ophthalmologists and quantified using fluorescence techniques. They can be the first clinical signs of macular degeneration.

Lipofuscin contains aggregations of A2E. Lipofuscin accumulates in RPE cells and poisons them by multiple known mechanisms. As RPE cells become poisoned, their biochemical activities decline and photoreceptors begin to degenerate. Extracellular drusen may further compromise RPE cells by interfering with their supply of vascular nutrients. Drusen also trigger inflammatory processes, which leads to choroidal neovascular invasions of the macula in one patient in ten who progresses to wet form AMD. Both the dry form and wet form progress to blindness.

"ERG" is an acronym for electroretinogram, which is the measurement of the electric field potential emitted by retinal neurons during their response to an experimentally defined light stimulus. ERG is a non-invasive measurement which can be performed on either living subjects (human or animal) or a hemisected eye in solution that has been removed surgically from a living animal.

As used herein, the term "RAL" means retinaldehyde. The term "RAL-trap" means a therapeutic compound that binds free RAL and thereby prevents the RAL from Schiff base condensation with membrane phosphatidylethanolamine (PE). "Free RAL" is defined as RAL that is not bound to a visual cycle protein. The terms "trans-RAL" and "all-trans-RAL" are used interchangeably and mean all trans retinaldehyde.

Figure 1:
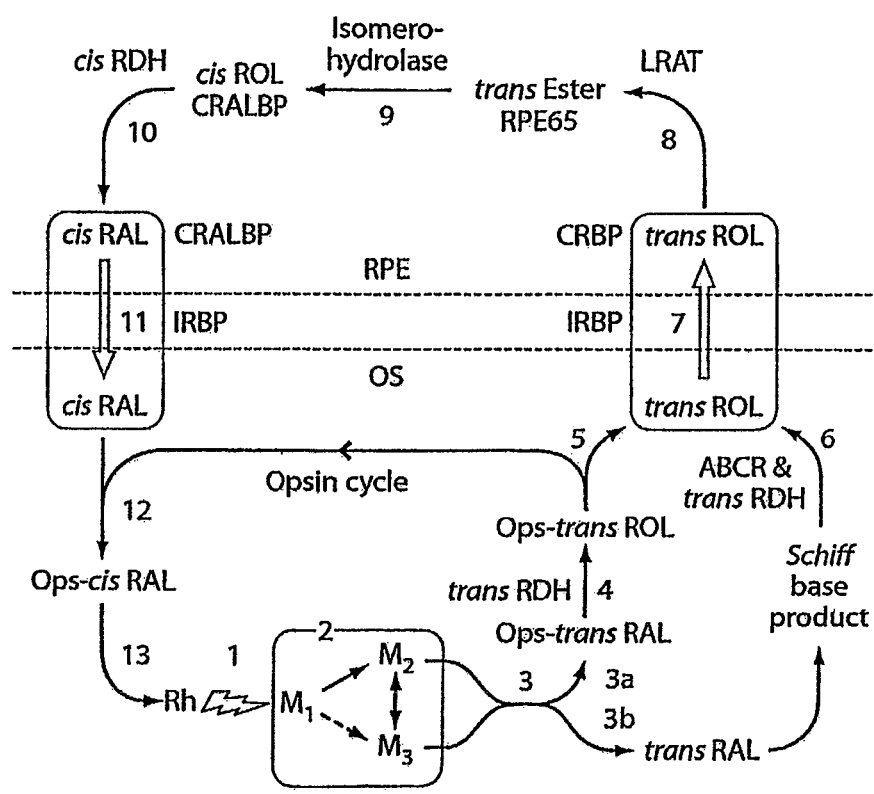
FIG. 1 is a schematic of the visual cycle.

A2E is a reaction by-product of a complex biochemical pathway called the "visual cycle" which operates collaboratively in both RPE cells and photoreceptor outer segments. The visual cycle recycles a photoreactive aldehyde chromophore called "retinaldehyde" which is derived from vitamin A and is essential for vision. In simplified terms, the visual cycle has four principal steps: 1) It converts vitamin A in the RPE into an aldehyde chromophore with one photoreactive strained double bond (11-cis-RAL); 2) It transports 11-cis-RAL to the retina where the it binds to a specialized photoreceptor protein called opsin; 3) Light photoisomerizes bound 11-cis-RAL to trans-RAL, which initiates the release of bound RAL from the opsin binding site; 4) It converts trans-RAL (an aldehyde) to vitamin A (an alcohol) and transports vitamin A back to the RPE where the cycle begins again. The pathway is illustrated in FIG. 1 which shows RPE cells on top and photoreceptor outer segments below (labeled "OS").

The aldehyde group of RAL helps bind the molecule to opsin by forming a reversible chemical bond to an amino acid sidechain in the opsin binding site. While the aldehyde group on RAL is essential for anchoring the molecule to the opsin binding site, it is otherwise hazardous because of its propensity to form Schiff bases with other biological amines. The reaction cascade for A2E formation is shown in FIG. 2. The first three reactions take place in photoreceptor outer segments and produce an intermediary product called A2PE. Once formed, A2PE partitions into lipid phase and accumulates in photoreceptor outer segment membranes. When RPE cells ingest discarded outer segments, their accumulated A2PE is routed to their lysosomes. The final reaction of FIG. 2 takes place inside RPE lysosomes and completes the formation of A2E.

As described above, macular degeneration and other forms of retinal disease whose etiology involves the accumulation of A2E and/or lipofuscin may be treated or prevented by lowering the amount of A2E formed. Compounds useful for doing so include RAL-traps. RAL-traps lower the amount of A2E formed, for example by forming a covalent bond with RAL that has escaped sequestering. RAL that has reacted with an RAL-trap compound is thereby unavailable to react with phosphatidyl ethanolamine.

Without wishing to be bound by theory, it is thought that treatment of a patient having AMD with an RAL-trap compound will reduce the rate of A2E formation without rate limiting the visual cycle, thereby avoiding the visual deficit of night blindness. In contrast, therapeutic agents for AMD treatment that reduce A2E synthesis are thought to rate-limit the visual cycle by competitive inhibition of retinoid binding sites of visual cycle proteins, whereby reduction in the turn-over rate of the visual cycle, causes a reduction in the formation rate of A2E. The present invention reduces A2E accumulation without competitive inhibition of retinoid binding sites on visual cycle proteins which is known to cause night blindness.

Figure 3:
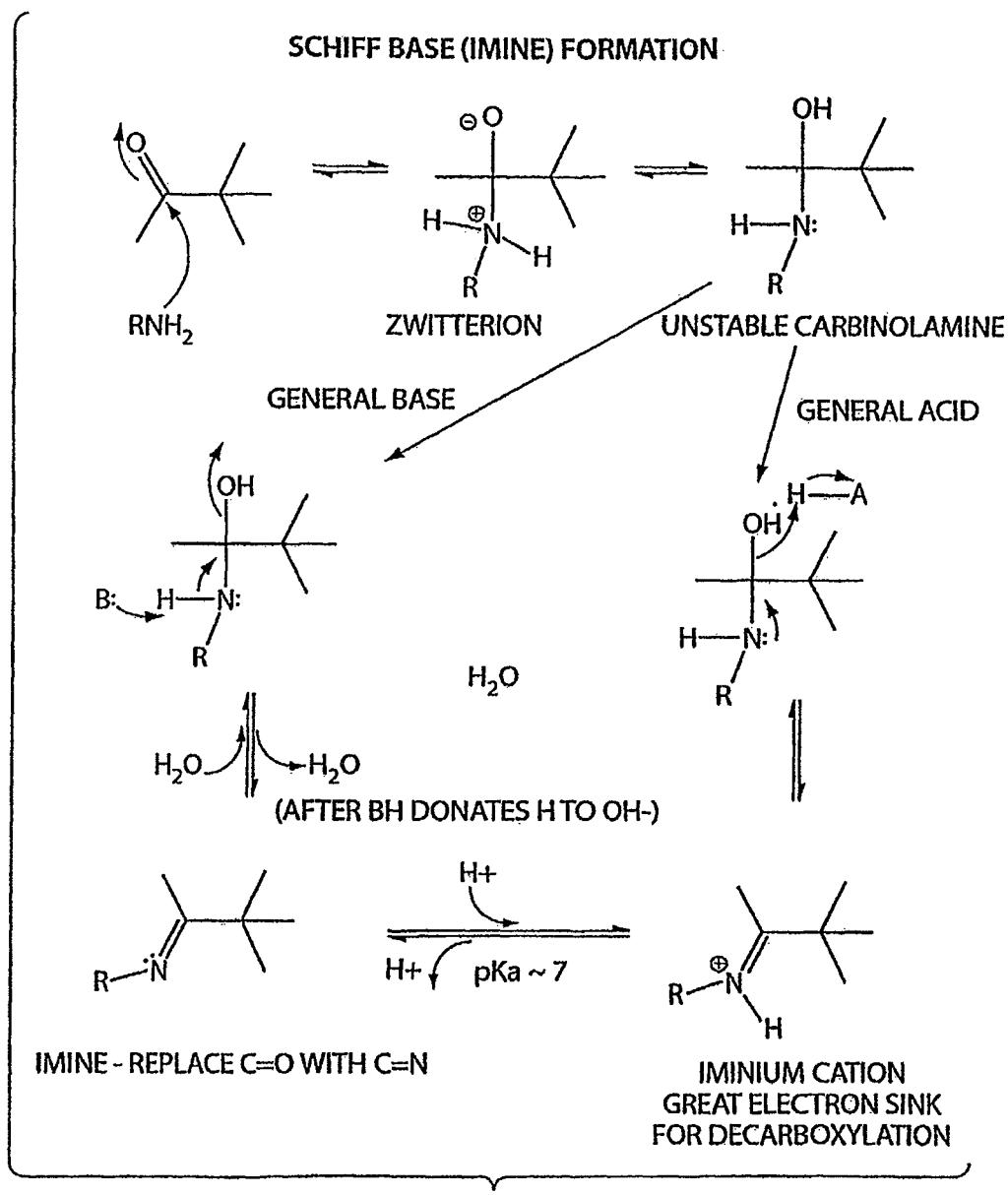
FIG. 3 is a schematic of Schiff base formation.

In certain embodiments, an RAL-trap is a compound known to form a reversible Schiff base adduct with RAL (FIG. 3).

RAL-traps of the invention include cyclic amines as well as 5- and 6-membered cyclic- and heterocyclic amines which may have one or more pairs of conjugated double bonds. In one example, the cyclic amines are aromatic.

Such compounds include, for example, aromatic amines, such as benzocaine:

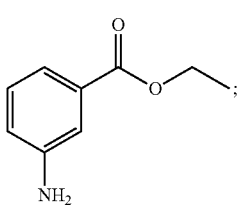

procaine:

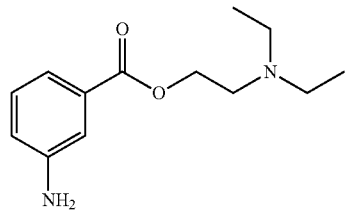 [SMILES: CCN(CC)CCOC(=O)c1cccc(N)c1]

orthocaine:

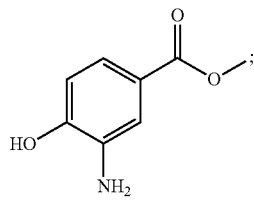

MS222 (6) (tricaine methane sulfonate)

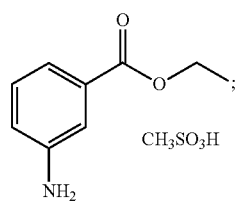

and methyl anthranilate:

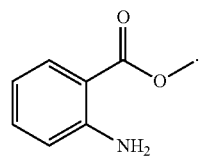

Heterocyclic compounds include

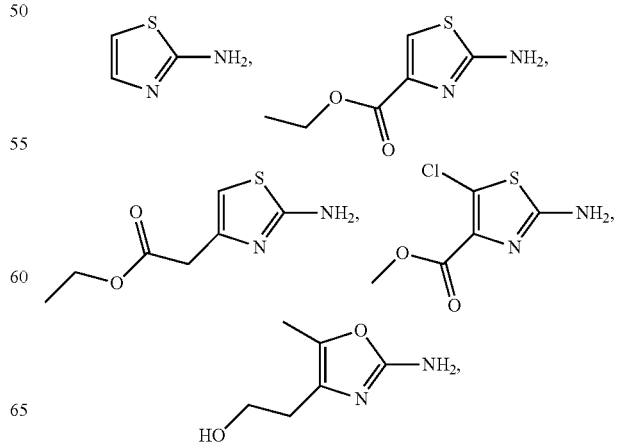

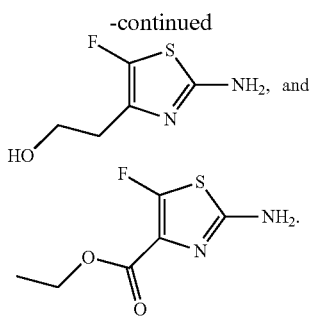

Useful controls for testing the effectiveness of RAL-traps are lidocaine, a local anesthetic that does not form a Schiff base, thus acting as a negative control; and darkness which slows or shuts down the visual cycle, as a positive control.

In one embodiment, the RAL-trap compound reacts with free RAL in a two-step fashion to form a stabilized adduct. For example, RAL and a primary amine of an RAL-trap compound condense to form a Schiff base adduct, and an internal cyclization reaction forms an uncharged ring which contains the amine nitrogen. This ring formation serves to stabilize the RAL adduct by making dissociation more unfavorable energetically. This prevents free RAL (i.e., RAL not bound to opsins or other proteins in the visual cycle) from being available to form Schiff base condensation products with phosphatidylethanolamine and thence prevents A2E formation. Further, once the ring closes, it prevents the amine nitrogen, now part of the ring, from condensing with a second RAL molecule. Reaction of the RAL-trap with a second RAL molecule is thought to be unfavorable, as such reaction would result in formation of an adduct having a structure similar to A2E, having dual RAL groups, with spayed tails which could cause lipid packing problems in biological membranes and therefore membrane detergency. Further, a reaction of the amine nitrogen with a second RAL would cause the nitrogen to become charged, which could cause unfavorable activity, including toxicity, such as poisoning the lysosomal proton pump in RPE cells.

Compounds useful as RAL-traps include those according to formula IV:

IV

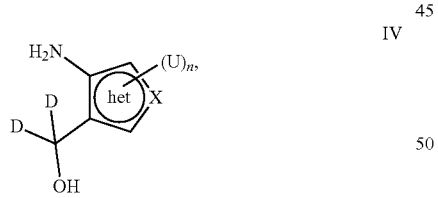

where X is O, N, N(H), or S, het is an optionally substituted 5 or 6-membered heterocycle, n is 0, 1, 2, or 3, and each D is an unbranched lower alkyl group. Each D can be the same or different.

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In one embodiment, each D is methyl.

In one embodiment, the ring substituent(s) (U) is chosen such that the $pK_a$ of the first ring $NH_2$ is approximately 3.5. Examples include the following ring systems with the $pK_a$ in parentheses:

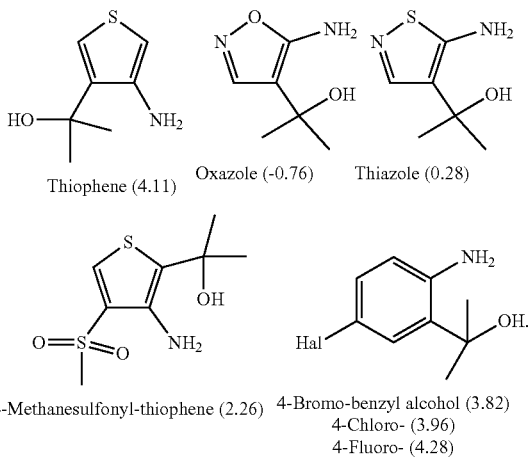

Thiophene (4.11)   Oxazole (-0.76)   Thiazole (0.28)

4-Methanesulfonyl-thiophene (2.26)   4-Bromo-benzyl alcohol (3.82)
4-Chloro- (3.96)
4-Fluoro- (4.28)

In one embodiment, such compounds react with RAL according to the mechanism depicted in Scheme 1:

Scheme 1

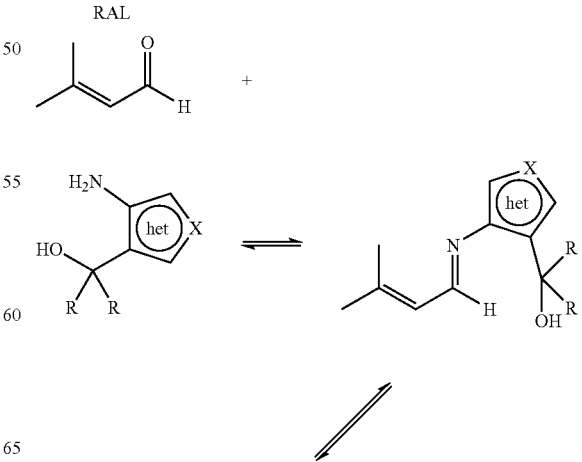

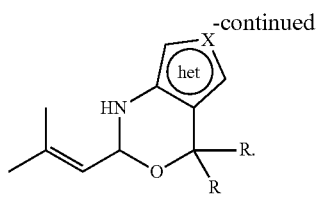

Compounds of formula IV,

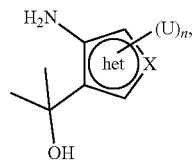

can be synthesized from the corresponding ester:

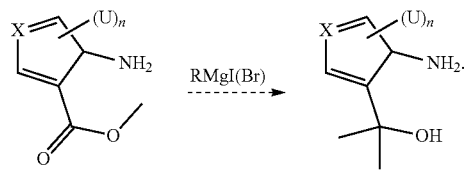

A depiction of the reaction between the compound

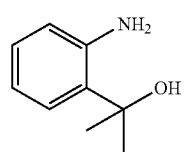

and RAL is presented in Scheme 2:

Scheme 2

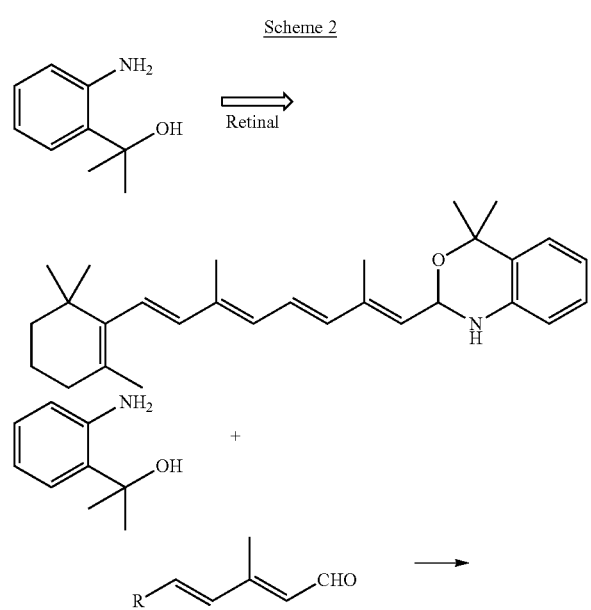

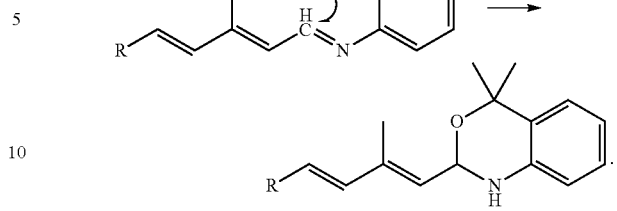

Compounds of the invention include RAL-traps having a 5- or 6-member ring. For example, the compounds of the invention preserve the absorption properties of 11-cis-RAL when the two compounds form a Schiff base adduct, i.e., that forming the adduct will not increase the extinction coefficient above that of free 11-cis-RAL nor shift its peak absorbance to a longer wavelength. Without being bound by theory, it is thought that this preservation of absorption properties will minimize treatment side effects on vision by protecting 11-cis-RAL from photoisomerization in the adduct state thereby preserving its chromophore activity should it subsequently dissociate from the adduct and re-enter the visual cycle where it will be available to bind to opsin in its photoactive state.

In certain embodiments, the RAL-trap of the invention is a compound having a structure represented by general formula I:

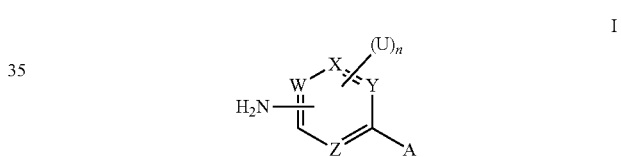

wherein, W, X, Y, and Z are each, independently, N, O, S, CU or CH, such that at least one of W, X, Y, and Z is N; n is 0, 1, 2, 3, or 4, A is

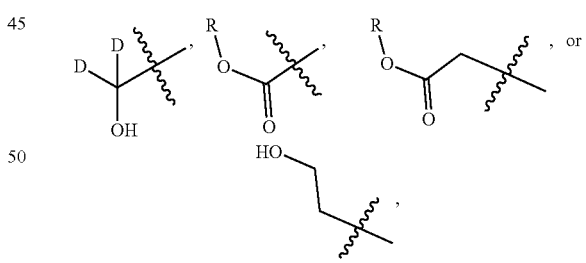

D is unbranched lower alkyl, and R is substituted or unsubstituted C1, C2, C3, C4, C5, C6, C7, or C8 straight chain alkyl, or substituted or unsubstituted C3, C4, C5, C6, C7 or C8 branched chain alkyl. Each D can be the same or different.

Substituents on the alkyl chain of R include a halogen atom; C1-C6 alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio.

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms.

In one example, U is aryl, for example benzene.

In certain compounds, A is

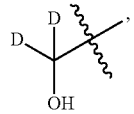

and D is methyl.

In certain compounds, U is a halo-substituted benzene.

In other compounds, two U substituents on adjacent carbon atoms are attached to form a 5 or 6 membered fused ring. Such rings are optionally substituted by groups selected from a halogen atom, hydroxyl, carbamoyl, aryl and amino. In certain compounds two adjacent U substituents can form a benzene. For example, such fused compounds have the structure Ia:

Ia

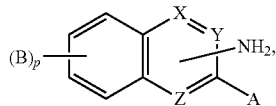

wherein X, Y, and Z are each, independently, N, O, S, CH, or absent, such that at least one of X, Y, and Z is N; p is 0, 1, 2, or 3, B is a halogen atom, hydroxyl, carbamoyl, aryl or amino, A is

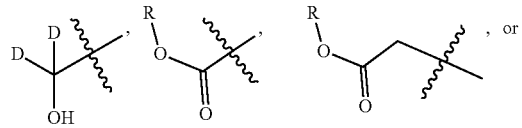

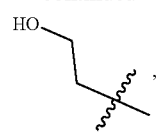

D is unbranched lower alkyl, and R is substituted or unsubstituted C1, C2, C3, C4, C5, C6, C7, or C8 straight chain alkyl, or substituted or unsubstituted C3, C4, C5, C6, C7 or C8 branched chain alkyl.

Examples of compounds of formula I include pyridine, pyridazine, pyrazine, and pyrimidine compounds.

Pyridazine compounds include:

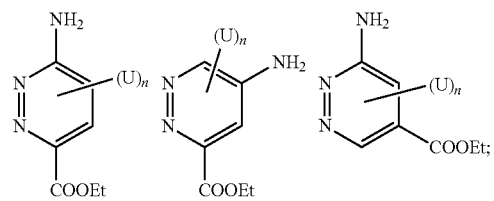

pyrazine compounds include:

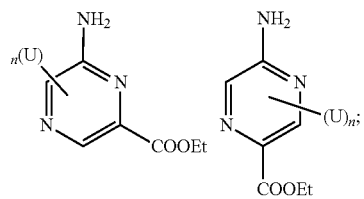

pyrimidine compounds include:

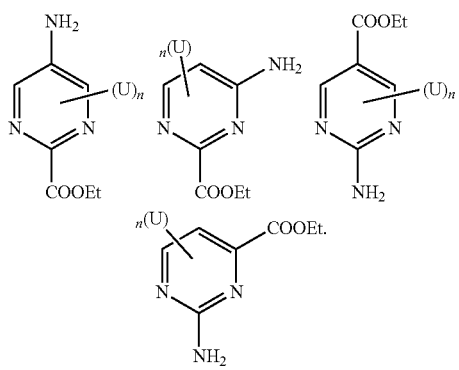

Compounds of formula I or Ia include:

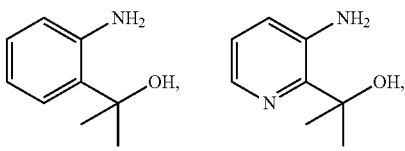

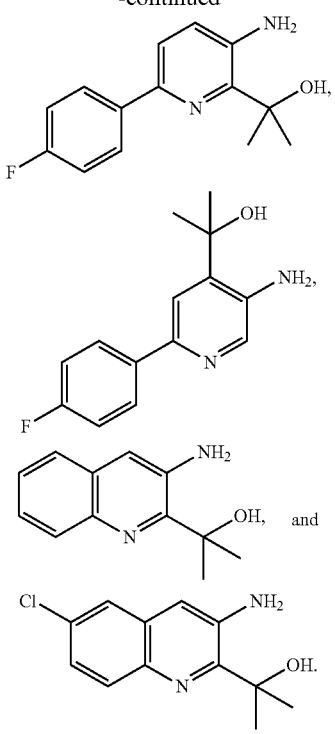

In certain embodiments, the RAL-trap of the invention is a compound having a structure represented by general formula II or IIa:

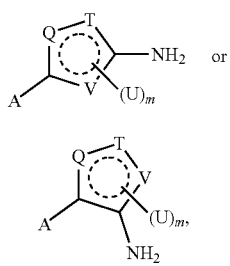

wherein, Q, T, and V are each, independently, N, NH, S, O, CU, or CH, such that at least one of Q, T and V is not CU or CH; the dashed ring represents two double bonds within the ring, which comply with the valency requirements of the atoms and heteroatoms present in the ring, m is 0, 1, or 2, A is

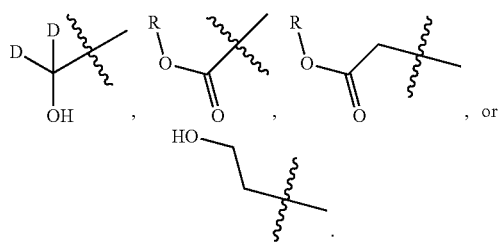

where D is unbranched lower alkyl, R is substituted or unsubstituted C1, C2, C3, C4, C5, C6, C7 or C8 straight chain alkyl, or substituted or unsubstituted C3, C4, C5, C6, C7 or C8 branched chain alkyl. For example, R is C2 alkyl (ethyl).

Substituents on the alkyl chain include a halogen atom; C1-C6 alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio.

U is a substituent selected from a halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. In one embodiment, example, U is alkyl. For example, U is methyl, ethyl, or propyl. In one embodiment, U is a halogen. For example, U is chloro, fluoro, or bromo. In certain compounds, two U substituents on adjacent carbon atoms are attached to form a 5 or 6 membered fused ring. Such rings are optionally substituted by groups selected from a halogen atom, hydroxyl, carbamoyl, aryl and amino.

In one example, U is aryl, for example benzene.
In certain compounds, A is

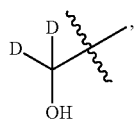

and D is methyl.

In certain compounds, U is a halo-substituted benzene.

Examples include furan and thiophene compounds, such as

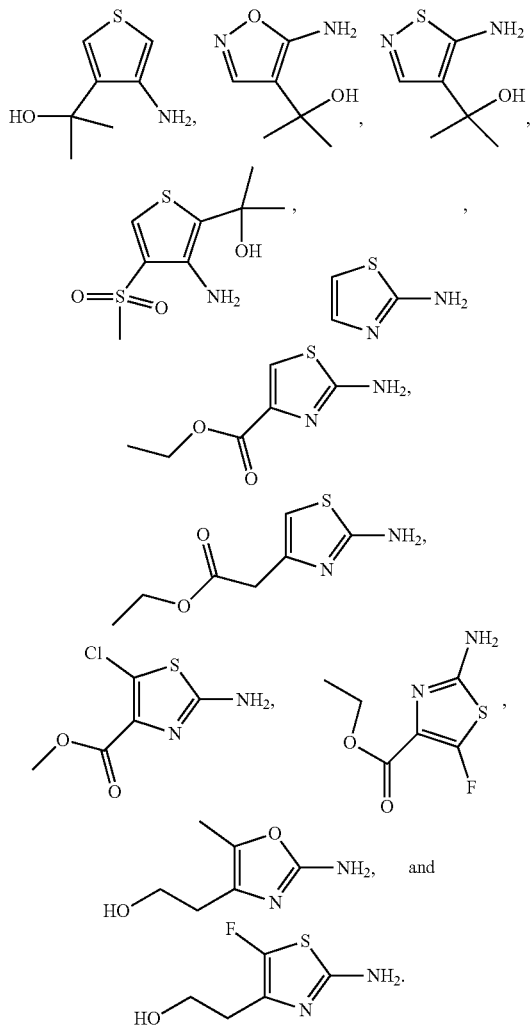

In certain embodiments, the RAL-trap of the invention is a compound having a structure represented by general formula III:

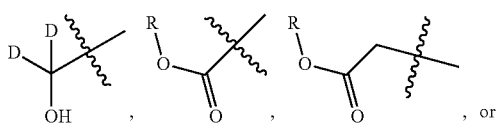

wherein, L is a single bond or CH$_2$; k is 0, 1, 2, 3, or 4; A is

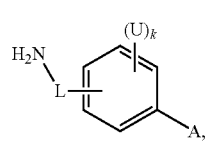, or

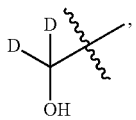

where D is unbranched lower alkyl, R is substituted or unsubstituted C1, C2, C3, C4, C5, C6, C7, or C8, straight chain alkyl, or substituted or unsubstituted C3, C4, C5, C6, C7, or C8, branched chain alkyl, k is 0, 1, 2, 3, or 4.

Substituents on the alkyl chain include a halogen atom; C1-C6 alkyl optionally substituted by a halogen atom, cyano, hydroxyl, carbamoyl, amino, formylamino, lower alkylcarbonylamino, aminosulfonylamino, or lower alkylthio; lower alkylcarbonyl wherein the alkyl portion of lower alkylcarbonyl is optionally substituted by a halogen atom, cyano, hydroxyl, carbamoyl, amino, formylamino, lower alkylcarbonylamino, aminosulfonylamino, or lower alkylthio; carbamoyl; or lower alkylthio wherein the alkyl portion of lower alkylthio is optionally substituted by a halogen atom, cyano, hydroxyl, carbamoyl, amino, formylamino, lower alkylcarbonylamino, aminosulfonylamino, or lower alkylthio.

U is a substituent selected from halogen atom; cyano; lower alkyl wherein one or more hydrogen atoms on the lower alkyl group are optionally substituted by groups selected from a halogen atom, hydroxyl, carbamoyl, amino, aryl, and a monocyclic or bicyclic heterocyclic group containing one or more hetero-atoms selected from nitrogen, oxygen, and sulfur atoms; lower alkylthio wherein one or more hydrogen atoms on the alkyl group are optionally substituted by groups selected from a halogen atom, hydroxyl, carbamoyl, amino, and aryl; lower alkylsulfonyl wherein one or more hydrogen atoms on the alkyl group are optionally substituted by groups selected from a halogen atom, hydroxyl, carbamoyl, amino, and aryl; hydroxyl; lower alkoxy; formyl; lower alkylcarbonyl; arylcarbonyl; carboxyl; lower alkoxycarbonyl; carbamoyl; N-lower alkylcarbamoyl; N,N-di-lower alkylaminocarbonyl; amino; N-lower alkylamino; N,N-di-lower alkylamino; formylamino; lower alkylcarbonylamino; aminosulfonylamino; (N-lower alkylamino)sulfonylamino; (N,N-di-lower alkylamino)sulfonylamino; aryl, optionally substituted by groups selected from a halogen atom, hydroxyl, carbamoyl, aryl and amino; and a monocyclic or bicyclic heterocyclic group containing one or more hetero-atoms selected from nitrogen, oxygen, and sulfur atoms. Examples include hydroxylamines and alkyl amine compounds.

In certain compounds, A is and D is methyl.

In certain compounds, U is a halo-substituted benzene.

In other compounds, two U substituents on adjacent carbon atoms are attached to form a 5 or 6 membered fused ring. Such rings are optionally substituted by groups selected from a halogen atom, hydroxyl, carbamoyl, aryl and amino. For example, such fused compounds have the structure IIIa:

IIIa

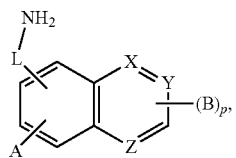

wherein X, Y, and Z are each, independently, N, O, S, CH CB, or absent, such that at least one of X, Y, and Z is N; p is 0, 1, 2, or 3, B is a halogen atom, hydroxyl, carbamoyl, aryl or amino, A is

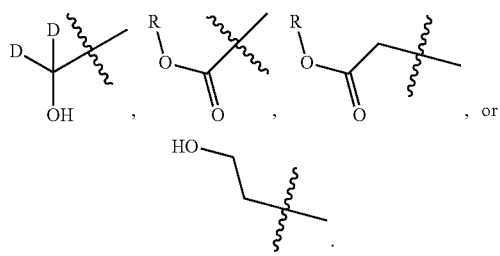

D is unbranched lower alkyl, R is substituted or unsubstituted C1, C2, C3, C4, C5, C6, C7, or C8 straight chain alkyl, or substituted or unsubstituted C3, C4, C5, C6, C7 or C8 branched chain alkyl, and L is a single bond or $CH_2$.

In some embodiments, two adjacent U substituents form a 6-membered fused heterocycle, for example, a pyridine ring. In other embodiments, two adjacent U substituents form 5-membered fused heterocycle. For example, two adjacent U substituents form a thiazole ring. In other embodiments, two adjacent U substituents form an oxazole ring. In other embodiments, two adjacent U substituents form an imidazole ring.

Examples of compounds of formula III or IIIa include:

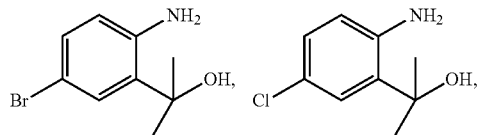

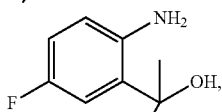

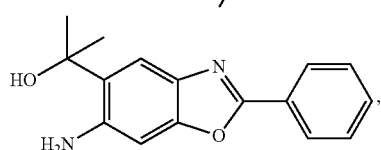

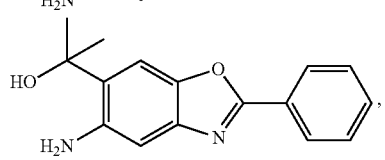

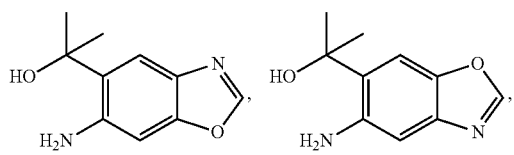

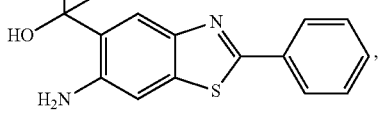

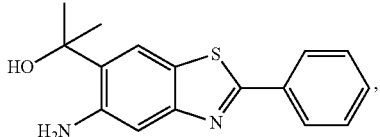

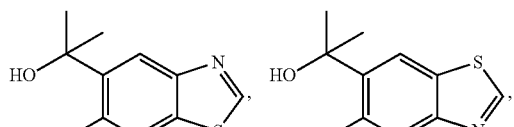

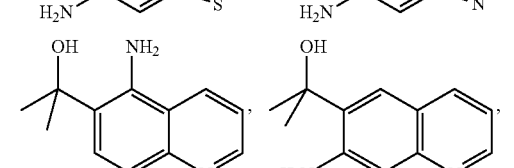

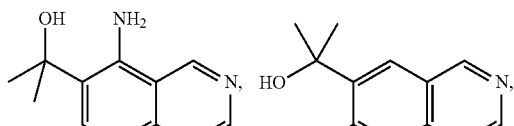

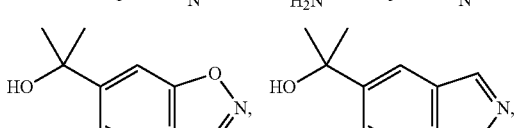

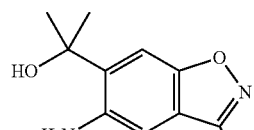

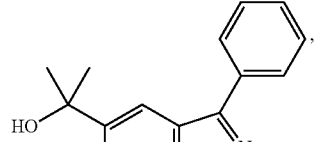

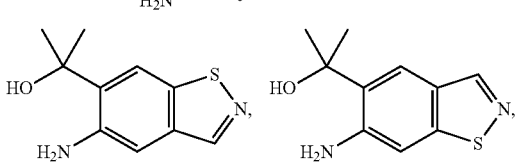

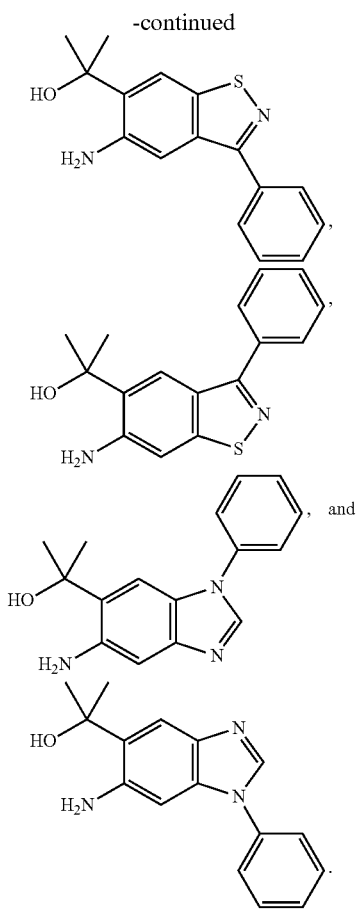

Reaction of the compound

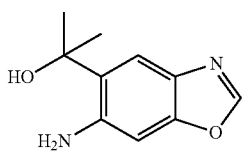

with RAL produces the following conjugate:

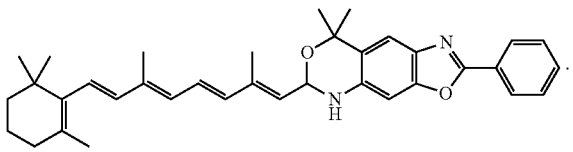 [SMILES: CC1=C(/C=C/C(C)=C/C=C/C(C)=C/C2Nc3cc4oc(-c5ccccc5)nc4cc3C(C)(C)O2)C(C)(C)CCC1]

Also included are pharmaceutically acceptable addition salts and complexes of the compounds of the formulas given above. In cases wherein the compounds may have one or more chiral centers, unless specified, the compounds contemplated herein may be a single stereoisomer or racemic mixtures of stereoisomers. Further included are prodrugs, analogs, and derivatives thereof.

Methods

As discussed above, a disclosed composition may be administered to a subject in order to treat or prevent macular degeneration and other forms of retinal disease whose etiology involves the accumulation of A2E and/or lipofuscin. Other diseases, disorders, or conditions characterized by the accumulation A2E may be similarly treated.

In one embodiment, a compound is administered to a subject that reduces the formation of A2E. For example, the compound may compete with PE for reaction with trans RAL, thereby reducing the amount of A2E formed. In another embodiment, a compound is administered to a subject that prevents the accumulation of A2E. For example, the compound competes so successfully with PE for reaction with trans RAL, no A2E is formed.

Individuals to be treated fall into three groups: (1) those who are clinically diagnosed with macular degeneration or other forms of retinal disease whose etiology involves the accumulation of A2E and/or lipofuscin on the basis of visual deficits (including but not limited to dark adaptation, contrast sensitivity and acuity) as determined by visual examination and/or electroretinography, and/or retinal health as indicated by fundoscopic examination of retinal and RPE tissue for drusen accumulations, tissue atrophy and/or lipofuscin fluorescence; (2) those who are pre-symptomatic for macular degenerative disease but thought to be at risk based on abnormal results in any or all of the same measures; and (3) those who are pre-symptomatic but thought to be at risk genetically based on family history of macular degenerative disease and/or genotyping results showing one or more alleles or polymorphisms associated with the disease. The compositions are administered topically or systemically at one or more times per month, week or day. Dosages may be selected to avoid side effects if any on visual performance in dark adaptation. Treatment is continued for a period of at least one, three, six, twelve or more months. Patients may be tested at one, three, six, twelve months or longer intervals to assess safety and efficacy. Efficacy is measured by examination of visual performance and retinal health as described above.

In one embodiment, a subject is diagnosed as having symptoms of macular degeneration, and then a disclosed compound is administered. In another embodiment, a subject may be identified as being at risk for developing macular degeneration (risk factors include a history of smoking, age, female gender, and family history), and then a disclosed compound is administered. In another embodiment, a subject may have dry AMD in both eye, and then a disclosed compound is administered. In another embodiment, a subject may have wet AMD in one eye but dry AMD in the other eye, and then a disclosed compound is administered. In yet another embodiment, a subject may be diagnosed as having Stargardt disease and then a disclosed compound is administered. In another embodiment, a subject is diagnosed as having symptoms of other forms of retinal disease whose etiology involves the accumulation of A2E and/or lipofuscin, and then the compound is administered. In another embodiment a subject may be identified as being at risk for developing other forms of retinal disease whose etiology involves the accumulation of A2E and/or lipofuscin, and then the disclosed compound is administered. In some embodiments, a compound is administered prophylactically. In some embodiments, a subject has been diagnosed as having the disease before retinal damage is apparent. For example, a subject is found to carry a gene mutation for ABCA4 and is diagnosed as being at risk for Stargardt disease before any ophthalmologic signs are manifest, or a subject is found to have early macular changes indicative of macular degeneration before the subject is aware of any effect on vision. In some embodiments, a human subject may know that he or she is in need of the macular generation treatment or prevention.

In some embodiments, a subject may be monitored for the extent of macular degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

In some embodiments, the disclosed methods may be combined with other methods for treating or preventing macular degeneration or other forms of retinal disease whose etiology involves the accumulation of A2E and/or lipofuscin, such as photodynamic therapy. For example, a patient may be treated with more than one therapy for one or more diseases or disorders. For example, a patient may have one eye afflicted with dry form AMD, which is treated with a compound of the invention, and the other eye afflicted with wet form AMD which is treated with, e.g., photodynamic therapy.

In some embodiments, a compound for treating or preventing macular degeneration or other forms of retinal disease whose etiology involves the accumulation of A2E and/or lipofuscin may be administered chronically. The compound may be administered daily, more than once daily, twice a week, three times a week, weekly, biweekly, monthly, bimonthly, semiannually, annually, and/or biannually.

The therapeutics may be administered by a wide variety of routes, as described above. In some embodiments, a compound may be administered orally, in the form of a tablet, a capsule, a liquid, a paste, and/or a powder. In some embodiments, a compound may be administered locally, as by intraocular injection. In some embodiments, a compound may be administered systemically in a caged, masked, or otherwise inactive form and activated in the eye (such as by photodynamic therapy). In some embodiments, a compound may be administered in a depot form, so sustained release of the compound is provided over a period of time, such as hours, days, weeks, and/or months. Preferably the compound is administered topically, as an eye drop formulation. Typical dose ranges include 0.5 to 5 mg/100 g for oral formulations and 0.5% to 5% solutions for eye drop formulations.

The compounds of the invention are provided in therapeutic compositions. The compound is present in an amount that is therapeutically effective, which varies widely depending largely on the particular compound being used. The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. The amount of compound incorporated into the composition also depends upon the desired release profile, the concentration of the compound required for a biological effect, and the length of time that the biologically active substance has to be released for treatment. In certain embodiments, the biologically active substance may be blended with a polymer matrix at different loading levels, in one embodiment at room temperature and without the need for an organic solvent. In other embodiments, the compositions may be formulated as microspheres. In some embodiments, the compound may be formulated for sustained release.

For oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

The compounds of the invention can also be administered in such oral dosage forms as timed release and sustained release tablets or capsules, pills, powders, granules, elixers, tinctures, suspensions, syrups and emulsions.

The compounds of the invention can also be administered topically, such as directly to the eye, e.g., as an eye-drop or ophthalmic ointment. Eye drops typically comprise an effective amount of at least one compound of the invention and a carrier capable of being safely applied to an eye. For example, the eye drops are in the form of an isotonic solution, and the pH of the solution is adjusted so that there is no irritation of the eye. In many instances, the epithelial barrier interferes with penetration of molecules into the eye. Thus, most currently used ophthalmic drugs are supplemented with some form of penetration enhancer. These penetration enhancers work by loosening the tight junctions of the most superior epithelial cells (Burstein, 1985, *Trans Ophthalmol Soc UK* 104(Pt 4): 402-9; Ashton et al., 1991, *J Pharmacol Exp Ther* 259(2): 719-24; Green et al., 1971, *Am J Ophthalmol* 72(5): 897-905). The most commonly used penetration enhancer is benzalkonium chloride (Tang et al., 1994, *J Pharm Sci.* 83(1): 85-90; Burstein et al., 1980, *Invest Ophthalmol Vis Sci.* 19(3): 308-13), which also works as preservative against microbial contamination. It is typically added to a final concentration of 0.01-0.05%.

Screening Methods

Suitable compounds may be identified by a variety of screening methods. For example, a candidate compound may be administered to a subject that has or is at risk of developing macular degeneration or other forms of retinal disease whose etiology involves the accumulation of A2E and/or lipofuscin, and the accumulation of a retinotoxic compound, such as A2E, can be measured. A drug that results in reduced accumulation of a retinotoxic compound compared to a control (absence of the drug) would thus be identified as a suitable drug.

Alternatively, RAL and RPE tissue may be analyzed for the presence of A2E and/or its precursors.

EXAMPLES

Example 1: Synthesis of Compounds

The compounds of the invention, and related derivatives, can be synthesized by methods known to one skilled in the art. For example, a detailed method for the synthesis of compound 7 is described below in Scheme 3.

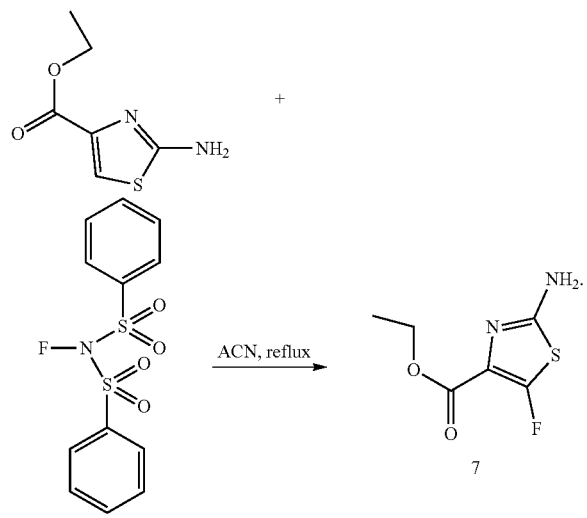

Scheme 3

A mixture of acetonitrile (60 mL) and ethyl 2-amino-1,3, thiazole-4-carboxylate (0.54 g, 3 mmol) and N-fluorobenzenesulfonimide (3.3 g, 9 mmol) was heated at reflux temperature for 18 hours. The color changed from yellow to reddish. The reaction mixture was concentrated and purified using chromatographic methods: column chromatography (2-5% methanol-chloroform), prep-TLC (2% methanol-chloroform), prep HPLC (column: Phenomenex Luna Phenyl-hexyl (150×4.6 mm ID, 3 μm packing), $\lambda_1$=215 nm, flow rate: 0.8 mL/min, injection volume: 5 mL, run time: 31 min, mobile phase gradient: A: water w 0.1% v/v TFA; B MeCN w 0.1% v/v TFA), and prep-TLC (10% meOH-chloroform) to afford a brown solid (380 mg). LCMS m/z: 145, 173, 191, 381, and 399. $^1$H NMR (300 MHz, CDCl$_3$) δ: 1.3 ppm (m, 3H Me) and 4.8 ppm (m, 2H, CH$_2$).

Example 2: In Vitro Schiff Base Confirmation

UV/VIS spectroscopy was used to monitor Schiff base condensation of RAL with the primary amine of a compound of the invention. The in vitro analysis of the Schiff base condensation product with RAL was performed for the disclosed compounds 1, 2, 3, 4, 5, and 6 and the results are shown in Table 1.

Figure 4A:
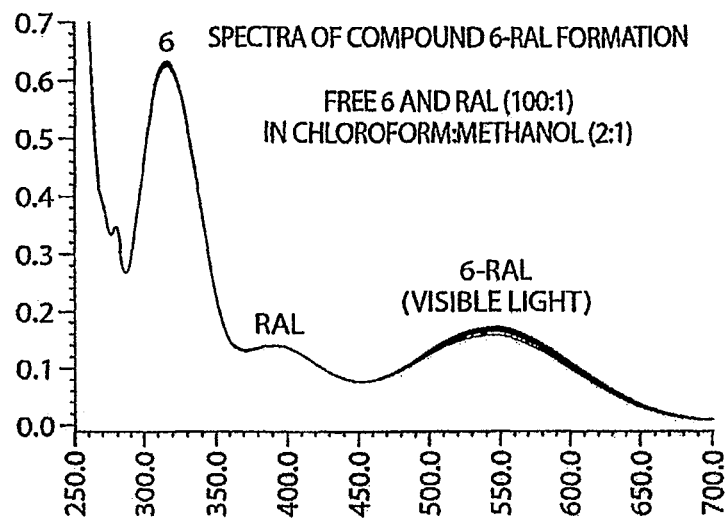
FIG. 4a is a UV-vis spectrum of compound 6 and RAL.
Figure 4B:
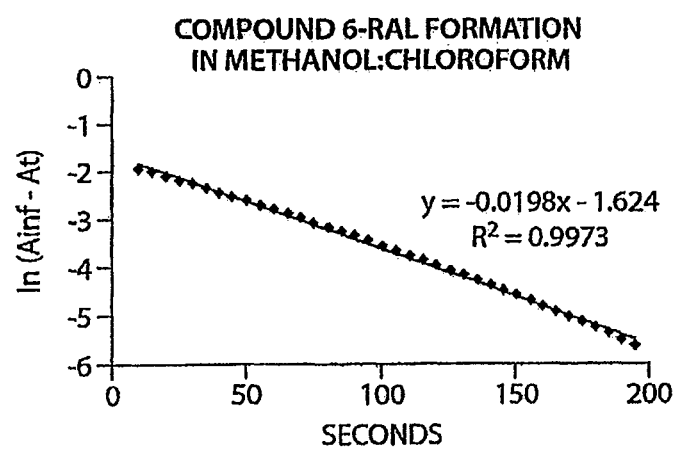
FIG. 4b is a graph of the formation of the Schiff base adduct.

In the solution phase analysis, the $\lambda_{max}$ value of both the free compound and the RAL Schiff base condensation product (RAL-SBC) are measured along with the value for tau of the RAL-SBC. As used herein, "RAL-SBC" means the Schiff base condensation product of RAL and a RAL-compound. Solution phase analysis is performed using a 100:1 mixture of compound and RAL using protocols known in the art. Several solvent systems were tested including aqueous, ethanol, octanol, and chloroform:methanol (various, e.g., 2:1). The solution kinetics are measured and found to be highly dependent on solvent conditions. FIGS. 4*a* and 4*b* show the results of Schiff base condensation of compound 6 and RAL (100:1) in chloroform:methanol (2:1).

Solid phase analysis of the Schiff base condensation is also performed using a 1:1 mixture of compound to RAL. The solid phase analysis is performed using protocols known in the art. The mixture is dried under nitrogen and condensation reaction occurs to completion.

Lipid phase analysis is performed using protocols known in the art and $\lambda_{max}$, tau (RAL-SBC vs. APE/A2PE), and competitive inhibition are measured. Liposome conditions are closer to in situ conditions.

Example 3: Log P and pKa Values

Log P values are shown in Table 1 for compounds 1, 2, 3, 4, 5, and 6. The partition coefficient (log P) is the log of the ratio [X$_{organic}$]/[X$_{aqueous}$] for a compound X at a pH where X at a pH where X is neutral, not ionized. Values above zero denote increasing lipophilic properties, and below zero, increasing hydrophilic properties. Octanol is commonly used as the organic solvent. Examples are as follows:

Log P=2 X is 10$^2$ more soluble in organic solvent than aqueous

Log P=0 X is equally soluble in both

Log P=−2 X is 10$^2$ more soluble in aqueous solvent then organic

Log P values are typically calculated algorithmically (not measured experimentally) by software programs such as Pallas and ACDlabs. Calculation results vary by software product and are regarded as order of magnitude approximations.

pKa values are shown in Table 1 for compounds 1, 2, 3, 4, 5, 6, and 7. pKa values are measured using known methods in the art. The acidity of a general acid, HA, is expressed by the chemical equation:

$$HA + H_2O \rightleftharpoons H_3O^+ + A^-$$

which is described by the equilibrium constant K. According to the general definition of an equilibrium constant, K is expressed as $$K = \frac{[H_3O^+][A^-]}{[HA][H_2O]}$$

Because, in aqueous solution, $[H_2O]$ will be constant at 55 moles $l^{-1}$, that number may be incorporated into a new constant Ka, defined as the acidity constant:

$$K_a = \frac{[H_3O^+][A^-]}{[HA]} \text{ moles } l^{-1}$$

This measurement when put in logarithmic scale is pKa=−log Ka. An acid with a pKa lower than 1 is defined as strong, one with a pKa higher than 4 is weak. The volume of distribution (V) of a drug may widely vary depending on the pKa of the compound. The volume of distribution relates to the amount of compound in the body to the concentration of compound in the blood or plasma.

TABLE 1

| ID | Structure | free λmax nm | RAL-SBC λmin nm | RAL-SBC tau sec | calculated logP vendor | calculated logP Pallas | calculated pKa NH₂ | pKa ring N |
|----|-----------|-------------|-----------------|-----------------|------------------------|------------------------|---------------------|------------|
| 1 | | 284 | 333 | 10,000 | 1.2 | 1.0 | — | 3.0 |
| 2 | | 294 | 340 | 3,000 | 1.3 | 0.5 | — | 2.1 |
| 3 | | 256 | 330 | 10,000 | 0.8 | 0.2 | — | 5.4 |
| 4 | | 260 | 325 | 10,000 | 1.4 | 0.9 | — | 4.5 |
| 5 | | 335 | 336 | 3,000 | 2.3 | 1.4 | 3.66 | n.a. |
| 6 | | 319 | 541 | 50 | 1.8 | 1.7 | 3.51 | n.a. |
| 7 | | — | — | — | n.a. | 1.2 | — | 2.7 |

Example 4: ERG Analysis of Dark Adaptation

Dark adaptation is the recovery of visual sensitivity following exposure to light. Dark adaptation has multiple components including both fast (neuronal) processes and slow (photochemical) process. Regeneration of visual pigment is related to the slow photochemical process. Dark adaptation rates are measured for several reasons. Night blindness results from a failure to dark adapt (loss of visual light sensitivity). It is possible to find a safe dose for night vision by measuring drug effects on dark adapted visual light sensitivity.

An electroretinogram (ERG) is used measure dark adaptation under normal vs. drug conditions. ERG is the measurement of the electric field potential emitted by retinal neurons during their response to an experimentally defined light stimulus. More specifically, ERG measures retinal field potentials at the cornea after a flash of light (e.g., 50 ms). Field strengths are $10^2$ to $10^3$ microvolts, originating in retinal cells.

ERG is a non-invasive measurement which can be performed on either living subjects (human or animal) or a hemisected eye in solution that has been removed surgically from a living animal. ERG requires general anesthesia which slows dark adaptation and must be factored into experimental design.

Figure 5:
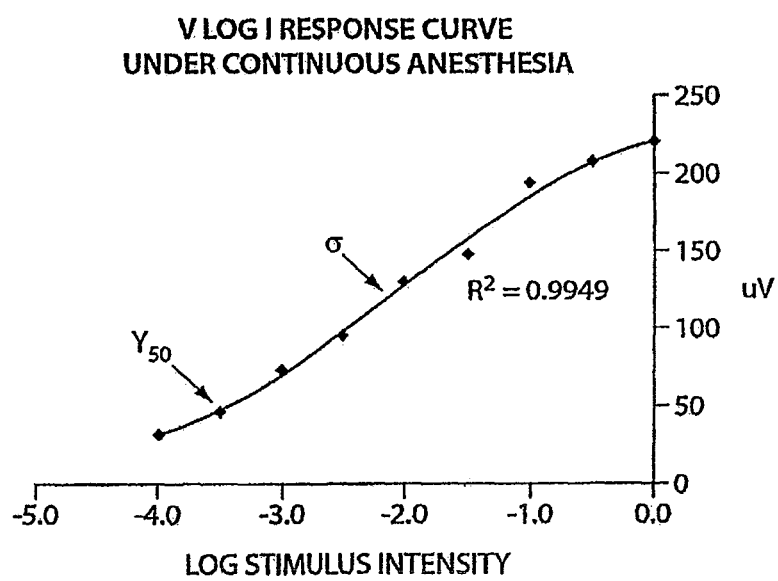
FIG. 5 is a graph of standard curve for ERG measurement of retinal responses to experimental stimuli of varying light intensity.

In a typical ERG analysis of dark adaptation experiment, every rat is dark adapted for hours to reach a consistent state of light sensitivity. The rat is then "photo-bleached," i.e., exposed briefly to light strong enough to transiently deplete the retina of free 11-cis-RAL (e.g., 2 min at 300 lux). The rat is then returned to dark immediately to initiate dark adaptation, i.e., recovery of light sensitivity due to regeneration of visual pigment. ERG is used to measure how quickly the rat adapts to dark and recovers light sensitivity. Specifically, a criterion response variable is defined for light sensitivity (see FIG. 5).

Figure 6A:
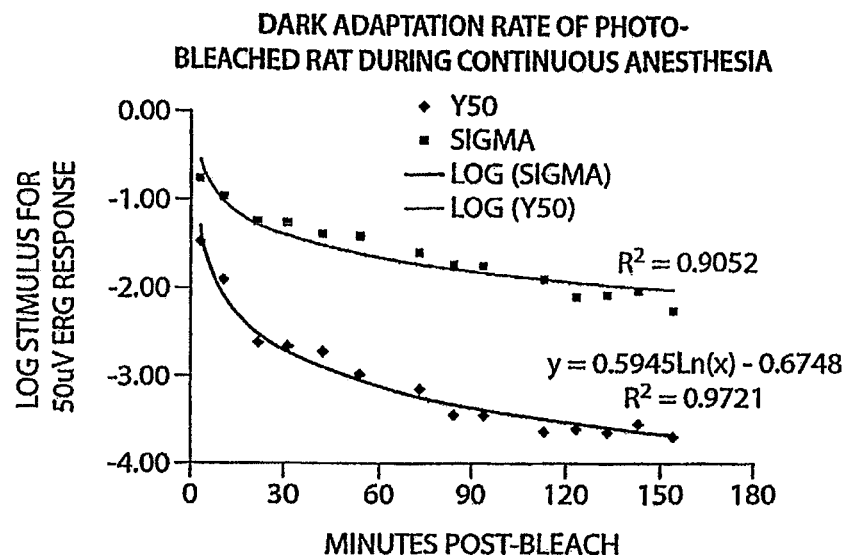
FIG. 6a is a graph of ERG measurement of the dark adaptation rate of a photo-bleached rat during anesthesia.
Figure 6B:
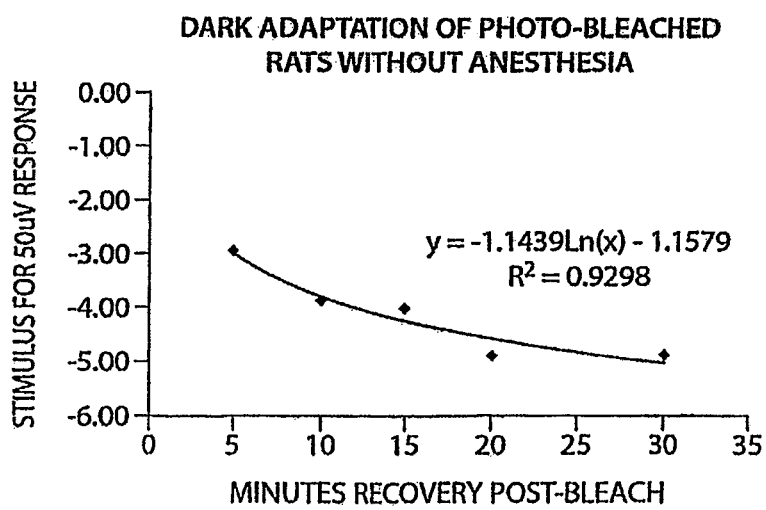
FIG. 6b is a graph of EGR measurement of the dark adaptation of a photo-bleached rat without anesthesia.

The ERG measurement is taken after a specific duration of post-bleach dark recovery (e.g., 30 min) determined previously by kinetic analysis (see FIGS. 6a and 6b). A curve fit is used to calculate value for the sensitivity variable. FIG. 6a shows recovery with anesthesia in the same rat including dark adaptation kinetics for $Y_{50}$ and σ. Slower adaptation is observed with less light sensitivity where $Y_{50}$ reaches −4.0 and tau=22.6 min. FIG. 6b shows recovery without anesthesia (5 different rats) including dark adaptation kinetics for $Y_{50}$. Faster adaptation is observed with more light sensitivity where $Y_{50}$ reaches −5.5 and tau=9.2 min.

Figure 7:
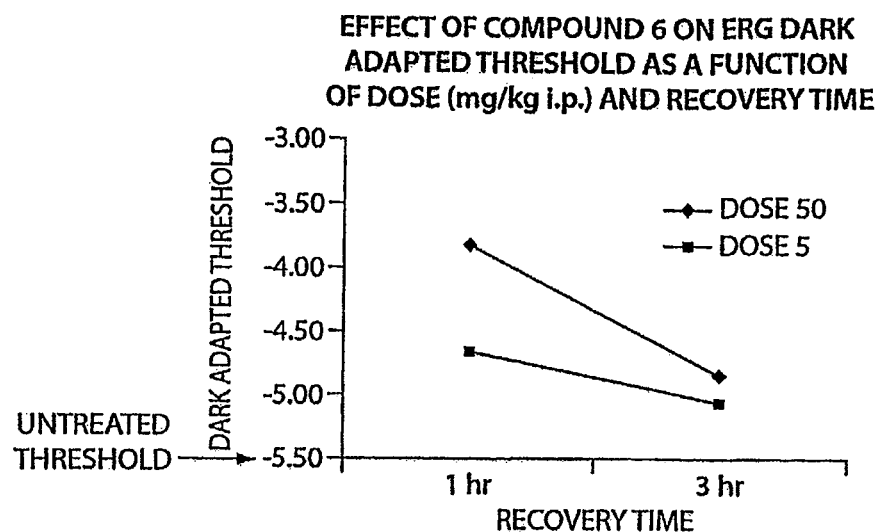
FIG. 7 is a graph of the effect of compound 6 on ERG light sensitivity of a dark-adapted rat.

The same paradigm as described above is followed for dose ranging. As shown below in FIG. 7, in the ERG dose ranging protocol, compound 6 i.p. lowers light sensitivity of dark adapted rats in a dose dependent manner. The effect on vision decreases after 3 hours.

Example 5: NMR Analysis of RAL Reactions

Figure 8:
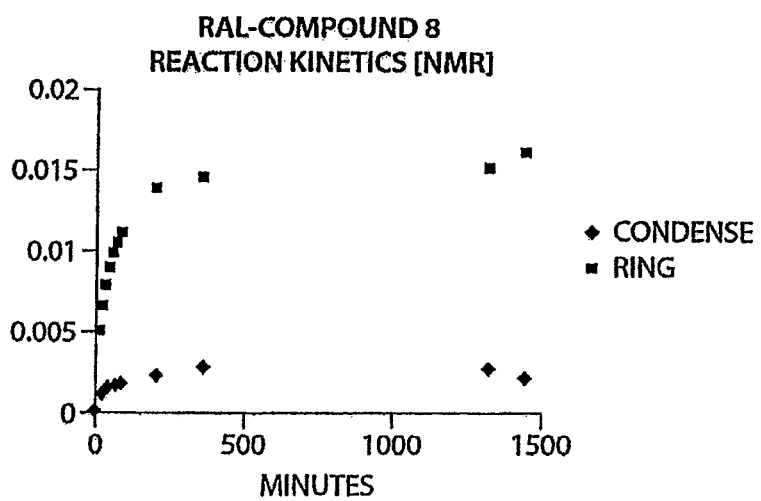
FIG. 8 is a graph showing RAL-compound 8 reaction kinetics by NMR.

NMR spectroscopy was used to monitor Schiff base condensation and ring formation of RAL with the primary amine of a compound of the invention. The NMR analysis of the RAL reactions was performed for the disclosed compounds 6, 8 and 9 as shown in FIG. 8 and Table 2. Condensation rates in pure chloroform are as follows: compound 6>8>9.

TABLE 2

| Compound # | Structure | tau (minutes) condense | ring |
|---|---|---|---|
| 6 | (ethyl 3-aminobenzoate) | 3 | n.a. |
| 8 | (2-(2-aminophenyl)propan-2-ol) | 122 | 109 |
| 9 | (6-chloro-2-(2-hydroxypropan-2-yl)quinolin-3-amine) | 320 | 568 |

Example 6: Inhibition of A2E Formation

This experiment is designed to establish proof of concept that chronic i.p. injection of a RAL-trap compound lowers the accumulation rate of A2E in wild type Sprague Dawley rats. These experiments compare the treatment efficacy of RAL-trap compounds to that of control compounds and lack of treatment.

Materials and Methods:

The study is performed with wild type Sprague Dawley rats. Rat treatment groups include for example, 8 rats of mixed gender per treatment condition. Each animal is treated with one of the following conditions:

Controls: (1) 13-cis retinoic acid to inhibit retinoid binding sites of visual cycle proteins as a protocol control, in that such treatment reduces the amount of free trans-RAL that is released and thereby available to form A2E, but with undesirable side effects of night blindness, and (2) a commercially available compound known clinically to modulate retinal function in humans and known experimentally to form a Schiff base adduct with free RAL, both in vitro and in vivo in animal models.

Vehicle
Compound
Untreated

A number of compounds are tested, e.g., 4 compounds. The compounds are tested across a dose range including 1, 5, 15, and 50 mg/kg. Treatment is administered daily for 8 weeks by i.p. injection.

Chemistry:

The experiments use a variety of chemistry services. For example, these experiments use commercially available compounds with analytical specification sheets to characterize the impurities. Compounds are also synthesized. Compounds are prepared in quantities sufficient for the required dosing. Formulations of the compound are suitable for use in initial animal safety studies involving intraperitoneal (i.p.) injection. The following three attributes of the Schiff base reaction product of trans-RAL with compounds of the invention are determined:

stability with respect to reaction rates
absorption properties, specifically uv-vis absorption maxima and extinction coefficients (see, e.g., FIG. 5 in Rapp and Basinger, *Vision Res.* 22:1097, 1982) or NMR spectral analysis of reaction kinetics
log P and log D solubility values e.g. calculated Biology and Biochemistry:

The experiments described herein use a variety of biology and biochemistry services. A "no effect level" (NOEL) dose of compounds of the invention for daily treatment with an eye drop formation is established, e.g., in the rabbit with an ocular irritation protocol and in the rodent with ERG measurement of dark adaptation in visual responses to light stimulation. After treatment and before eye enucleation, the following non-invasive assays are performed in animals, e.g., rabbits:

RPE and photoreceptor cell degeneration, as evident by fundus photography (Karan, et al., 2005, *PNAS* 102: 4164)

Extracellular drusen and intracellular lipofuscin as measured by fundus fluorescent photography (Karan et al., 2005)

Light responses are characterized by ERG (Weng, et al., *Cell* 98:13, 1999). Intracellular A2E concentration of retinal RPE cell extracts is measured in all treated animals upon the conclusion of the treatment protocol using an analytical method such as those described by Karan et al., 2005; Radu et al., 2003; and Parish et al., *PNAS* 95:14609, 1998. For example, in a sample of treated animals, one eye is assayed, and the other eye is saved for histology analysis (as described below). In the remaining animals, both eyes are assayed separately for A2E formation.

In the post-treatment eyes set aside for histology (as described above), the morphology of retinal and RPE tissue is assessed with light microscopy histology techniques (Karan et al., 2005, with the exception that electron microscopy is not used in the experiments described herein).

The safety of the treatment regimen is assessed for example using a combination of:

Daily documented observation of animal behavior and feeding habits throughout the treatment period Visual performance as measured by ERG at the end of the treatment period Ocular histology at the end of the treatment period.

INCORPORATION BY REFERENCE

The entire disclosure of each of the patent documents, including certificates of correction, patent application documents, scientific articles, governmental reports, websites, and other references referred to herein is incorporated by reference in its entirety for all purposes. In case of a conflict in terminology, the present specification controls.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

We claim:

1. A method of treating macular degeneration in a subject, the method comprising administering to the subject a compound of the following structure:

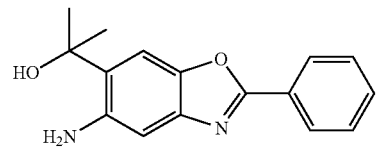 [SMILES: CC(C)(O)c1cc2oc(-c3ccccc3)nc2cc1N]

or a pharmaceutically acceptable salt thereof.

2. The method of claim 1, wherein the macular degeneration is age related macular degeneration (AMD).

3. The method of claim 2, wherein the AMD is wet AMD.

4. The method of claim 2, wherein the AMD is dry AMD.

5. The method of claim 1, wherein the macular degeneration is Stargardt's disease.

6. The method of claim 1, wherein the compound is administered topically to the eye of the subject.

7. The method of claim 1, wherein the compound is administered as an eye-drop or ophthalmic ointment.

8. The method of claim 1, wherein the compound is administered by intraocular injection.

9. The method of claim 8, wherein the compound is

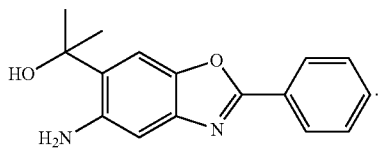 [SMILES: CC(C)(O)c1cc2oc(-c3ccccc3)nc2cc1N]

\* \* \* \* \*